US009894888B2

(12) United States Patent
Garcia et al.

(10) Patent No.: US 9,894,888 B2
(45) Date of Patent: Feb. 20, 2018

(54) TRANSGENIC IMMUNODEFICIENT MOUSE EXPRESSING HUMAN SIRP-ALPHA

(71) Applicant: Institut Pasteur, Paris (FR)

(72) Inventors: Sylvie Garcia, Arcueil (FR); Malika Serra-Hassoun, Charenton-le-Pont (FR)

(73) Assignee: INSTITUT PASTEUR, Paris (FR)

(*) Notice: Subject to any disclaimer, the term of this patent is extended or adjusted under 35 U.S.C. 154(b) by 0 days.

(21) Appl. No.: 14/388,108

(22) PCT Filed: Mar. 26, 2013

(86) PCT No.: PCT/EP2013/056443
§ 371 (c)(1),
(2) Date: Sep. 25, 2014

(87) PCT Pub. No.: WO2013/144165
PCT Pub. Date: Oct. 3, 2013

(65) Prior Publication Data
US 2015/0056636 A1 Feb. 26, 2015

(30) Foreign Application Priority Data
Mar. 26, 2012 (EP) ..................................... 12305351

(51) Int. Cl.
| | | |
|---|---|---|
| A01K 67/027 | (2006.01) | |
| C07K 14/705 | (2006.01) | |
| C12N 15/85 | (2006.01) | |
| C07K 14/74 | (2006.01) | |
| G01N 33/50 | (2006.01) | |

(52) U.S. Cl.
CPC ...... *A01K 67/0278* (2013.01); *A01K 67/0271* (2013.01); *C07K 14/70503* (2013.01); *C07K 14/70539* (2013.01); *C07K 14/70596* (2013.01); *C12N 15/8509* (2013.01); *G01N 33/5088* (2013.01); *A01K 2207/12* (2013.01); *A01K 2207/15* (2013.01); *A01K 2217/052* (2013.01); *A01K 2217/15* (2013.01); *A01K 2217/206* (2013.01); *A01K 2227/105* (2013.01); *A01K 2267/03* (2013.01); *A01K 2267/0331* (2013.01); *A01K 2267/0337* (2013.01); *A01K 2267/0381* (2013.01); *C12N 2800/107* (2013.01); *G01N 2500/10* (2013.01)

(58) Field of Classification Search
USPC .............................................. 800/3, 18, 21, 2
See application file for complete search history.

(56) References Cited

FOREIGN PATENT DOCUMENTS

| WO | 03/018744 A2 | 3/2003 |
| WO | 2005/067709 A2 | 7/2005 |
| WO | 2008/010099 A2 | 1/2008 |
| WO | 2008/010100 A2 | 1/2008 |
| WO | WO 2008/010099 | * 1/2008 |
| WO | WO 2008/010100 | * 1/2008 |

OTHER PUBLICATIONS

Strowig (PNAS, Aug. 9, 2011, vol. 108, No. 32, p. 13218-13223, and Supplemental Material).*
Shultz (Nature Rev., Feb. 2007, vol. 7, No. 2, p. 118-130).*
Manz (Nature Immunol., Oct. 2009, vol. 10, No. 10, p. 1039-1042).*
Shultz (Annals NY Acad of Sci, Dec. 2011, vol. 1245, p. 50-54).*
Barclay, Neil A. et al, "Signal regulatory protein alpha /CD47 interaction and function," Current Opinion in Immunology, vol. 21, pp. 47-52 (2009).
Garcia, Sylvie et al, "Humanized mice: current states and perspective," Immununology Letters, vol. 146, pp. 1-7 (2012).
Takenaka, Katsuto et al, "Polymorphism in Sira modulates engraftment of human hennatopoietic stem cells", Nature Immunology, vol. 8, pp. 1313-1323 (2007).
Legrand, Nicolas et al., "Functional CD47/signal regulatory protein alpha (SIRPa) interaction is required for optimal huan T- and natural killer—(NK) cell homeostasis in vivo," Proc. Natl. Acad. Sci. U.S.A., vol. 108(32); pp. 1324-1329 (2011).
Linder, Carol Cutler, "Genetic Variables That Influence Phenotype," ILAR J., vol. 47(2), pp. 132-140 (2006).
Manz, Markus G., Renaissance for mouse models of human hematopoiesis and immunobiology, Nat Immunol., vol. 10(10), pp. 1039-1042 (2009).
Schultz, Leonard D. et al., "Humanized mice in translational biomedical research," Nat. Rev. Immunol., vol. 7(2), pp. 118-130 (2007).
Shultz, Leonard D et al., "Humanized mice as a preclinical tool for infectious disease and biomedical research," Annals of the New York Academy of Sciences, vol. 1245, pp. 50-54 (2011).
Strowig, Till et al., "Transgenic expression of human signal regulatory protein alpha in Rag2 -/- gammac -/- mice improves engraftment of human hematopoietic cells in humanized mice," Proc. Nat. Acad. Sci. USA, vol. 108(32), pp. 13218-1323 (2011).
Willinger, Tim et al., "Improving human hemato-lymphoid-system mice by cytokine knock-in gene replacement", Trends in Immunology, vol. 32, No. 7, pp. 322-323 (2011).
Macchiarini, F. et al., "Humanized Mice: Are we there yet'?" JEM, vol. 202, No. 10, pp. 1307-1311 (2005).

(Continued)

*Primary Examiner* — Michael Wilson
(74) *Attorney, Agent, or Firm* — Arrigo, Lee & Guttman LLP

(57) ABSTRACT

The present invention provides a transgenic mouse which comprises a deficiency for murine T lymphocytes, B lymphocytes and NK cells, a deficiency for murine MHC class I and MHC class II molecules, and a functional xenogenic SIRPα transgene. This mouse is useful for in vivo screening of various compounds, including immuno-therapeutic agents and vaccines. The said mouse is also useful for testing the in vivo metabolism of xenobiotic compounds.

8 Claims, 11 Drawing Sheets

(56) References Cited

OTHER PUBLICATIONS

Figure 1:
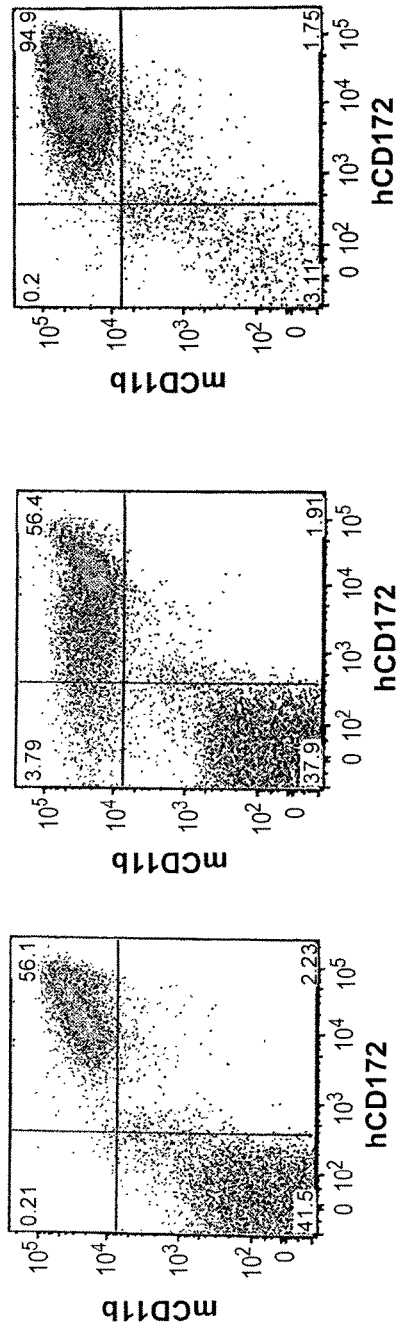

Garcia .S, "Limits of the Human-PBL-SCID Mice Model: Severe Restriction of the Vb T-Cell Repertoire of Engrafted Human T Cells," Blood, vol. 89, No. 1, pp. 329-336 (1997).
Ridgway, W. M. et al, "New tools for defining the 'genetic background' of inbred mouse strains," Nature Immunology, vol. 8, No. 7, pp. 669-673 (2007).
Anthony Rongvaux et al., "Human thrombopoietin knockin mice efficiently support human hematopoiesis in vivo," PNAS USA, vol. 108, No. 6, pp. 2378-2383 (2011).
Elisabetta Traggiai, et al., "Development of a Human Adaptive Immune System in Cord Blood Cell-Transplanted Mice," Science vol. 304, pp. 104-107 (2004).
Julien Villaudy, "Challenging Development of a Humanized Mouse Model for Evaluating the HTLV-1 Infection and Leukemogenic Process in vivo," Dec. 22, 2011.

\* cited by examiner

NP_001035111

MEPAGPAPGRLGPLLCLLLAASCAWSGVAGEEELQVIQPDKSVLVAAGETATLRCTATSLIPVGPIQWFRGAGPGRELIYNQKEGHFPRVTTVSDLTKRNNMDFSIRIGNITPADA
GTYYCVKFRKGSPDDVEFKSGAGTELSVRAKPSAPVVSGPAARATPQHTVSFTCESHGFSPRDITLKWFKNGNELSDFQTNVDPVGESVSYSIHSTAKVVLTREDVHSQVICEVAH
VTLQGDPLRGTANLSETIRVPPTLEVTQQPVRAENQVNVTCQVRKFYPQRLQLTWLENGNVSRTETASTVTENKDGTYNWMSWLLVNVSAHRDDVKLTCQVEHDGQPAVSKSHDLK
VSAHPKEQGSNTAAENTGSNERNIYIVVGVVCTLLVALLMAALYLVRIRQKKAQGSTSSTRLHEPEKNAREITQDTNDITYADLNLPKGKKPAPQAAEPNNHTEYASIQTSPQPAS
EDTLTYADLDMVHLNRTPKQPAPKPEPSFSEYASVQVPRK"

FIGURE 6

NM_001040022

TCCGGCCCGCACCCCAAGAGAGGGCCTTCAGCTTTGGGGCTCAGAGAGGCACGACCTCCTGGGAGGGTTAAAAGGCAGAGCGCCCCCGCGCCCCCGCCCCGAC
TCCTTCGCCGCCTCCAGCCTTCGCCAGTGGAAGCGGGGAGCGGGCCGAGTCCGAGGGGAGGTCGGCCGCCGAACTTCCCCGGTCCGAACTTCCCGGCCCCCGAC
TAGCCAGTCGCGCTGACCTTAGAAACAAGTTTGCGCAAGTGGAGCGGCCCGCCTCGGGCGCCTTGCCTGCCGGCGAGTGGCGGGTGAGGAGGAGCTGCA
CAGCCGCGGCCATGAGAGCCCCGACCCGCCGGAATCTGCAGCTGGACACCACTCTGCCGTGACTCTGATCCTGTGGGGCCATCCAGTGGTTCAGAGGAGCTGGAC
GGTGATTCAGCCTGACAAGTCCGTGTTGGTTGCAGCTGGGACAGCCACTTGTTCAGACCTGTTCAGAACATGTTTCATCGCACTTTCATCGCATCGGTAACATCACC
CAGGCCGGGAATTAATCTACAATCAAAGAAGAGGCCACTTCCCCCGGGTAACAACTGTTTCAGACCTGTTCAGACGTGGAGTTTAAGTCTGAGACAGCAGGCCCGATGACGTGGAGTTTAAGTCTGAGACAGCAGCCAATCACCCTGAAATGTTCAAAAATGGGAATG
CCAGGCAGATGCCGGCACCTACTGTGTGAAGTTCCGGAGGCCCACACAGTGAGCTGAGTTTAAGTCTGAGACGTGGAGTTTAAGTCTGAGACAGCAGCCAATCACCCTGAAATGTTCAAAAATGGGAATG
CGTGGTATCGGCCCTGCGGCGAGGGCCACAACGTGACCCCCGTAGGAGAGAGACCCTCTTCGTGGGACTGGAAGTTCTACCCCAGACTACAGCCTGTGCTGACCGCAGCAGCATCCACAGAAGACATCACCCGAGAGCGTGCACCTGTGCTGACCGCAGCAGTTTACCTCTCAAGTCATCTGC
GAGGTGGCCGACTTCACCGTCACCGTCGAGGGGAGACCCCTCTTCGTGGGACTGGAAGTTCTACCCCAGACTACAGCCTGTTGGAGAATGCTGACCTGTTGGAGAATGTGAAGCTCACCTGCAGCGATGAACGGGCAGCCAGCGTCAGCAAAGC
CCAGGTGAATGTACCTACAACTGGATGAGCTGCTCTGCCGAAGGCTCAATGATATCGCCACAGGGATGATGTATCTGCCCACAGGGATGATGTATCTGCCCACAGGGATGATGTATCTGCCCACAGGGATGAATGTCTCACCTGCAGCGAACATCTATATTGTGTGGGTGTGCAGAAATAACAC
AGGATGACCTGAAGGTCTCAGCGACGGCCAGGCTCAAATCAGACAGAGAAAGCCCAGGCTGCTGAAGCTGCTCAACCTGACCTATGCGAACATGTCCGAATCAGACAGAGAAAGCCCAGGCTGCTGAAGCTGCTCAACCTGACCTATGCGAACATGTGCGAGAAGTGCAACACGAGTATGCCAGCATTCAGAGTACGCCAGCGT
GTTGGCCCTACTGATGGCGGCCCTCTACCTCGCGAACCTGCCGAATCAGACAGAGAAAGCCCAGGCTGCTGAAGCTGCTCAACCTGACCTATGCGAACATGTGCGAGAAGTGCAACACGAGTATGCCAGCATTCAGAGTACGCCAGCGT
AGGACACAAATGATATCACATATCACACACCTCGGAGGAAGTGAATGGGACCAGTTGGTCAAGCTGAGGAAGCTGCTTTCCCCCATTCTCTTGTCCCCAAGCGACCTTTCTGTGCTCTCCAAGGAGCAGCAGCCGCCGTGATGATGAGCCACGCGCGTGGGCAGCCACGGCCCTCGTCCCCCCATTGCCACAT
CAGCCGCGTGCTCCGAGGAAGTGAATGGGACCAGTTGGTCAAGCTGAGGAAGCTGCTTTCCCCCATTCTCTTGTCCCCAAGCGACCTTTCTGTGCTCTCCAAGCTGCCTGGGGCCCAGGGGCCACCAGCAGCCCGGAACTGTTCGTGTGCCCAAGACTCTTGTGCTGTGGGTTTTGAAGACC
TGGGGCGGTGCCAGGCTGACGTTGCCAAGGACCAGGGAACCAGCAGCCGAGCCTGATCTTCCAGGGTGGGGAGGAGAAAATCCACCTCCACCACCTTCCCCCTGACCTCCACCACCTTCCATGGGAGAGAGAGACCATGAGTCCTGGAGAGCCATGAGTCCTCCCGTTCCCATGTGGTTTGTGCCTCTGCCTCCATCACCATGTGGTTTGAAGACC
ACCTGAGAGGTGCCTCCCCCGATGCTCCGAAGCCTGACTCTTCCAGGGTGGGAAGATTTCCCCTTTAGATGAAGATTTCCCCTTTAGATGCTAAAAGACCCATGAGTCCTGGAGAGACCATGAGTCCTGGAGAGACCATGAGTCCTCCCTTCCATGAAACTGGAGAAGTCCTGGAGAGACCATGAGTCCTCCCTTGCGTTCCTTGGTGAGGTT
CTGCCAACAGTCCTGGGCTGCCCAACTGTGTTGCCCAACTGTGTTCCCAACTGTGTCCCCCAAGTGTTGCCCAACTGTGTCCCCCAAGTGTTGCCCAACTGTGTCCCCCAAGTGTTCCCCAAGTGTTGCCCAACTGTGTCCCCAAGTGTTGCCCTAGACCTGAGCTTGCCCTGAGAGACCTGAGCTTGCCCTGGGGCCTGTGGACGCCTGTAAAT
CAAGACTCCTGGGCTGCCCAACTGTGTTGCCCAACTGTGTTCCCAACTGTGTCCCCAAGTGTTGCCCAACTGTGTCCCCCAAGTGTTGCCCAACTGTGTCCCCCAAGTGTTCCCCAAGTGTTGCCCAACTGTGTCCCCAAGTGTTGCCCTAGACCTGAGCTTGCCCTGAGAGACCTGAGCTTGCCCTGGGGCCTGTGGACGCCTGTGTCTGTC
TACTGAGAAATGTGAAACTGCAATCTTGTAATCTTGTGAGGTCTTTGTGAGGTCTTTGTGAGGTCTTTGTGTTTTTTCTTAAACAACAGCAACGTGAGTTCCTCCAAGACTTGAGTTCCTCCAAGACTTGAGTTCCTCCAAGAA
ATGTGTTGAAGTCCATGGTTGGGTCTTGTTGGGTCTTGTGAAGTCTGAGGAAAGTTTAACAGTTTCTGGCTGGGACTGTTCTGGCTGGGACTGTTCTGGCTGGGACTGTTCTGCAGTCTCAGGCTGGGACTGTTCTCAGCCCGCAGCCATGTTCCCATGTGTTCCCATGTGTTCCCATGTGTTCCCATGTGTTCCCATGTGTTCCCAGCCTTCTGTGACCCCG
TGGGCAAGAAGGATCAGGTCAGCCTCACTCCCTGGAGACACAGCCTTCTGGAGACACAGCCTTCTGGAGACACAGCCTTCTGGAGACACAGCCTTCTGCCTTCTGGAGACACAGCCTTCTGGAGACACAGCCTTCTGGAGACACAGCCTTCTGGAGACTTCTGCTGACTGACTTGCTCTGCTCAGTTCTGCTCAGTGTCCAGCTTGTGACCCCCAGCTCCAGCTCAGTTCTGCTCAGTGTCCAGCTTGTGACCCCCAGCTCCAGCTCAGTTCTGCTCAGTGTCCAGCTTGTGACCCCCAGCTCGTGCTCAGTGTCCAGCTCGTGCTCAGTGTCCAGCTCAGTTCTGCTCAGTGTCCAGCTTGTGACCCCCAGCTCGTGACCCCCAGCTCGTGCTCAGTGTCCAGCTCGTGCTCAGTGTCCAGCTCGTGCTCAGTGTCCAGCTCAGTTCTGCTCAGTGTCCAGCTTGTGACCCCCAGCTCGTGCTCAGTGTCCAGCTCAGTTCTGCTCAGTGTCCAGCTTGTGACCCCCAGCTCGTGCTCAGTGTCCAGCTCGTGCTCAGTGTCCAGCTCAGTTCTGCTCAGTGTCCAGCTCAGTTCTGCTCAGTGTCCAGCTTGTGACCCCCAGCTCGTGCTCAGTGTCCAGCTTGTGACCCCCAGCTCCTGGACTGTCAGTGCAGTGCAGTAGTGGGGATAGTGAAGATGACA
CCCCTCCCCCACCAGCTCTCTCATAAGACACTTTAGGAACACACAGAGGGTAGGGATCAAAACTGAATAAATTGAAGACAACAGAAACCCCCACCCTCTATCGCCCGTCATCGTGGCCGGTATCCGGCCGTCATCCGGGGCCGTCGTGCGGGGCCGTCGTGACCATCCGTGCCCGGGGGAGCTGGGGCCGGGGCCGTCGTGAGCAGGGGCCGGGGCCGTCGGGGCCAAGCCTGACCTCCGCCGGGCTGACCTCCGCCGGGCTGACCTCCGCCGGGCTGACCTCCGCCGGGCTGACTCCGGCCGGGCTGACCTCCGCCTGGGCCTGGGCTGACCTCCGCCGGCCTCCGTGCGGGGCCGTCGTGAGCTGGGGCCTGTTCCCCTC
TGTCCCAGAGAAGTTGCCAGAGGGTGTGACCAATCTCTGCTCCATTTTCTGCTCCAAAGAGCCATTTTCTGCTCCAAAGAGGGTGGATCAAAACTTGTCCAAACTTGTCCAGTCGCTAATTGAAATATCAATAAATGATAAATGATAAAACTGAATCAAAACTGAATAAAGTTCAGTCGCTAAATTCAGTCGCTAAATTTAAGGATGTCCGGCTGTGAAGCTGCGGCTGTGGAAGCTGCGGCTGTGGAAGCTGCGGCTGTGGAAGCTGCAGATGGTGCAGATGGTGCAGATGTGTCGGCTGTGAAGCTGCGGCTGTGGGCTGATTTCCCCTC
TGTCCCAGAGAAGTTGCCAGAGGGTGTGACCAATCTCTGCTCCATTCTGCTCCATTCTGCTCCATTCTGCTCCATTCTGCTCCATCGCCGTCATCGTGAAGCTGTGAAGCTGTGAAGCTGTGAAGCTGCGGCTGTGGAAGCAGATGTGTCAGCTGTGGGAAGCAGATGTGTCAGCTGTGGGATGAAGCAGATGTGTCAGCTGTGGATGAAGCAGATGTGTCAGCTGTGGCTCGGGCTGTGAAGCTGCAGATGTGGCAGATGTGTCAGCTGTGGATGAAGCAGATGTGTCAGCTGTGGGCTCGGGCTGTGAAGCTGCAGATGTGGCAGATGTGTCAGCTGTGGATGAAGCAGATGTGTCAGCTGTGGGCTCGGGCTGTGAAGCTGCAGATGTGGCAGATGTGTCAGCTGTGGATGAAGCAGATGTGTCAGCTGTGGGATGAAGCAGATGTGGCAGATGTGGCAGATGTGGCAGATGTGGCAGATGTGTCAGCTGTGGCTCGGGCTGTGAAGCTGCAGATGTGGCAGATGTGGCAGATGTGGCAGATGTGGCAGATGTGGCAGATGTGGCAGATGTGGCAGATGTGGCAGATGTGGCAGATGTGGCAGATGTGGCAGATGTGTCAGCTGTGGCTCGGGCTGTGAAGCTGCAGATGTGGCAGATGTGGCAGATGTGGCAGATGTGGCAGATGTGGCAGATGTGTCAGCTGTGGCTCGGGCTGTGAAGCTGCTGGCTGGTCGCAGCTGTGAAGCTGCTGGCTGGTCGCAGCTGTGAAGCTGCTGGCTGGTCGCAGCTGTGAAGCTGCTGGCTGGTCGCAGCTGTGAAGCTGCTGGCTGGTCGCAGCTGTGAAGCTGCTGGCTGGTCGCAGCTGTGAAGCTGCAGATGTGTCAGCTGTGGCTCGGGCTGTGAAGCTGCAGATGTGGCAGATGTGGCAGATGTGGCAGATGTGGCAGATGTGGCAGATGTGGCAGATGTGGCAGATGTGGCAGATGTGGCAGATGTGGCAGATGTGGCAGATGTGGCAGATGTGGCAGATGTGTCAGCTGTGGATGAAGCAGATGTGTCAGCTGTGGCTCGGGCTGTGAAGCTGCAGATGTGTCAGCTGTGGCTCGGGCTGTGAAGCTGCTGAGCTGATTTCTGATTCCCCCTC
TTCAGTCTTCACTATAACTCTTAGAGTTGAGAGTTGAGATTGCATGTTCATAATGTTCATGTTCATAATGTTCATGTTCATAATGTTCATGTTCATAATGTTCATGATGACTCCTGGCCTTGGGATGATGCTAATGTTCATGATGTTCATGATGACTCCTGGCCTTGGGATGACTCCTGGCCTTCGGCCTGAGCTGGGCTGTAAAAGTAGCTGAGCTGTAAAAGTAGCTGAGCTGTAAAAGTAGCTGAGCTGTAAAAGTAGCTGAGCCATCCTGCCCAT

FIGURE 7

TCCTGGAGGTCCTACAGGTGAAACTGCAGGAGCTCAGCATAGACCCAGCTCTCTGGGGATGGTCACCTGGTGATTCAATGATGCATCCAGGAATTAGCTGAGCCAACAGACCA
TGTGGACAGCTTTGGCCAGAGCTCCCGTGTGCAGAGCTCGGCATCTGGGAGCCACCAGTGACCCTGGCTCAGGCTAGTTCCAAATTCCAAAAGATTGGCTTGTAAACCTTCGTCTCCCT
CTCTTTTACCCAGAGACAGCACACATACGTGTGCACACGCATGCAACGGCATCACACAACATTCAGTATTTAAAAGAATGTTTTCTTGGTGCCATTTTCATTTTATTTTATTTTAATTCTTGG
AGGGGAAATAAGGGAATAAGGCCAAGAAGATGTATAGCTTTAGCTTGCTGGCAACCTGTGTATTGAACCCAGGAAGGAAGAGTCGAACC
AACCCTGCGGAAGGAGCATGGTTTCAGGAGTTTATTTTAAGACTGCTGGGAAGGAAACAGGCCCCATTTTGTATATAGTGCAACTAAACTTTTTGGCTTGCAAAATATTTTGT
AATAAAGATTTCTGGGTAATAATGA

FIGURE 7 (cont'd)

SEQUENCE LISTING

```
<160> NUMBER OF SEQ ID NOS: 2

<210> SEQ ID NO 1
<211> LENGTH: 504
<212> TYPE: PRT
<213> ORGANISM: Homo sapiens
<220> FEATURE:
<221> NAME/KEY: misc_feature
<223> OTHER INFORMATION: Homo sapiens signal-regulatory protein alpha
      (SIRPA)

<400> SEQUENCE: 1

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300
```

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
            325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
            405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
            485                 490                 495

Ala Ser Val Gln Val Pro Arg Lys
            500

<210> SEQ ID NO 2
<211> LENGTH: 4201
<212> TYPE: DNA
<213> ORGANISM: Homo sapiens
<220> FEATURE:
<221> NAME/KEY: misc_feature
<223> OTHER INFORMATION: Homo sapiens signal-regulatory protein alpha
      (SIRPA)

<400> SEQUENCE: 2
tccggcccgc acccaccccc aagaggggcc ttcagctttg gggctcagag gcacgacctc      60
ctggggaggg ttaaaaggca gacgcccccc cgccccccgc gccccgcgc cccgactcct     120 tcgccgcctc cagcctctcg ccagtgggaa gcggggagca gccgcgcggc cggagtccgg     180
aggcgagggg aggtcggccg caacttcccc ggtccacctt aagaggacga tgtagccagc     240
tcgcagcgct gaccttagaa aaacaagttt gcgcaaagtg gagcggggac ccggcctctg     300
ggcagccccg gcggcgcttc cagtgccttc cagcccctcgc gggcggcgca gccgcggccc     360
atggagcccg ccggcccggc ccccggccgc ctcgggccgc tgctctgcct gctgctcgcc     420
gcgtcctgcg cctggtcagg agtggcgggt gaggaggagc tgcaggtgat tcagcctgac     480
aagtccgtgt tggttgcagc tggagagaca gccactctgc gctgcactgc gacctctctg     540
atccctgtgg ggcccatcca gtggttcaga ggagctggac caggccggga attaatctac     600
aatcaaaaag aaggccactt ccccggggta acaactgttt cagacctcac aaagagaaac     660
aacatggact tttccatccg catcggtaac atcaccccag cagatgccgg cacctactac     720
tgtgtgaagt tccggaaagg gagccccgat gacgtggagt taagtctgg agcaggcact     780 gagctgtctg tgcgcgccaa accctctgcc ccgtggtat cgggccctgc ggcgagggcc     840

```
acacctcagc acacagtgag cttcacctgc gagtcccacg gcttctcacc cagagacatc    900
accctgaaat ggttcaaaaa tgggaatgag ctctcagact tccagaccaa cgtggacccc    960
gtaggagaga gcgtgtccta cagcatccac agcacagcca aggtggtgct gacccgcgag   1020
gacgttcact ctcaagtcat ctgcgaggtg gcccacgtca ccttgcaggg ggaccctctt   1080
cgtgggactg ccaacttgtc tgagaccatc cgagttccac ccaccttgga ggttactcaa   1140
cagcccgtga gggcagagaa ccaggtgaat gtcacctgcc aggtgaggaa gttctacccc   1200
cagagactac agctgacctg gttggagaat ggaaacgtgt cccggacaga aacggcctca   1260
accgttacag agaacaagga tggtacctac aactggatga gctggctcct ggtgaatgta   1320
tctgcccaca gggatgatgt gaagctcacc tgccaggtgg agcatgacgg gcagccagcg   1380
gtcagcaaaa gccatgacct gaaggtctca gcccacccga aggagcaggg ctcaaatacc   1440
gccgctgaga acactggatc taatgaacgg aacatctata ttgtggtggg tgtggtgtgc   1500
accttgctgg tggccctact gatggcggcc ctctacctcg tccgaatcag acagaagaaa   1560
gcccagggct ccacttcttc tacaaggttg catgagcccg agaagaatgc cagagaaata   1620
acacaggaca caaatgatat cacatatgca gacctgaacc tgcccaaggg gaagaagcct   1680
gctccccagg ctgcggagcc caacaaccac acggagtatg ccagcattca gaccagcccg   1740
cagcccgcgt cggaggacac cctcacctat gctgacctgg acatggtcca cctcaaccgg   1800
acccccaagc agccggcccc caagcctgag ccgtccttct cagagtacgc cagcgtccag   1860
gtcccgagga agtgaatggg accgtggttt gctctagcac ccatctctac gcgctttctt   1920
gtcccacagg gagccgccgt gatgagcaca gccaacccag ttcccggagg gctggggcgg   1980
tgcaggctct gggacccagg ggccaggtg gctcttctct ccccaccccct ccttggctct   2040 ccagcacttc ctgggcagcc acggccccct ccccccacat gccacatac ctggaggctg    2100 acgttgccaa accagccagg gaaccaacct gggaagtggc cagaactgcc tggggtccaa   2160
gaactcttgt gcctccgtcc atcaccatgt gggttttgaa gacccttcgac tgcctccccg   2220 atgctccgaa gcctgatctt ccagggtggg gaggagaaaa tcccacctcc cctgacctcc   2280
accacctcca ccaccaccac caccaccacc accaccacta ccaccaccac ccaactgggg   2340
ctagagtggg gaagatttcc cctttagatc aaactgcccc ttccatggaa aagctggaaa   2400
aaaactctgg aacccatatc caggcttggt gaggttgctg ccaacagtcc tggcctcccc   2460
catccctagg ctaaagagcc atgagtcctg gaggaggaga ggacccctcc caaaggactg   2520
gagacaaaac cctctgcttc cttgggtccc tccaagactc cctggggccc aactgtgttg   2580
ctccacccgg acccatctct cccttctaga cctgagcttg cccctccagc tagcactaag   2640
caacatctcg ctgtggacgc ctgtaaatta ctgagaaatg tgaaacgtgc aatcttgaaa   2700
ctgaggtgtt agaaaacttg atctgtggtg ttttgttttg ttttttttct taaaacaaca   2760
gcaacgtgat cttggctgtc tgtcatgtgt tgaagtccat ggtttgggtct tgtgaagtct   2820 gaggtttaac agtttgttgt cctggaggga ttttcttaca gcgaagactt gagttcctcc   2880
aagtcccaga accccaagaa tgggcaagaa ggatcaggtc agccactccc tggagacaca   2940
gccttctggc tgggactgac ttggccatgt tctcagctga gccacgcggc tggtagtgca   3000
gccttctgtg acccgctgt ggtaagtcca gcctgcccag ggctgctgag ggctgcctct    3060
tgacagtgca gtcttatcga gacccaatgc ctcagtctgc tcatccgtaa agtggggata   3120
gtgaagatga caccctccc caccacctct cataagcact ttaggaacac acagagggta    3180
gggatagtgg ccctggccgt ctatcctacc cctttagtga ccgcccccat cccggctttc   3240
```

```
tgagctgatc cttgaagaag aaatcttcca tttctgctct caaaccctac tgggatcaaa    3300
ctggaataaa ttgaagacag ccaggggat ggtgcagctg tgaagctcgg gctgattccc    3360
cctctgtccc agaaggttgg ccagagggtg tgacccagtt acccttaac ccccaccctt    3420 ccagtcgggt gtgagggcct gaccgggccc agggcaagca gatgtcgcaa gccctattta    3480
ttcagtcttc actataactc ttagagttga gacgctaatg ttcatgactc ctggccttgg    3540
gatgcccaag ggatttctgg ctcaggctgt aaaagtagct gagccatcct gcccattcct    3600
ggaggtccta caggtgaaac tgcaggagct cagcatagac ccagctctct gggggatggt    3660
cacctggtga tttcaatgat ggcatccagg aattagctga gccaacagac catgtggaca    3720
gctttggcca gagctcccgt gtggcatctg ggagccacag tgacccagcc acctggctca    3780
ggctagttcc aaattccaaa agattggctt gtaaaccttc gtctccctct cttttaccca    3840
gagacagcac atacgtgtgc acacgcatgc acacacacat tcagtatttt aaaagaatgt    3900
tttcttggtg ccattttcat tttatttat tttttaattc ttggaggggg aaataaggga    3960
ataaggccaa ggaagatgta tagctttagc tttagcctgg caacctggag aatccacata    4020
ccttgtgtat tgaaccccag gaaaaggaag aggtcgaacc aaccctgcgg aaggagcatg    4080
gtttcaggag tttattttaa gactgctggg aaggaaacag gccccatttt gtatatagtt    4140
gcaacttaaa cttttggct tgcaaaatat ttttgtaata aagatttctg ggtaataatg    4200
a                                                                    4201
```

TRANSGENIC IMMUNODEFICIENT MOUSE EXPRESSING HUMAN SIRP-ALPHA

INTRODUCTION

Many vaccines are currently being developed for human cancer immunotherapy and for treatment of infectious diseases, such as malaria, AIDS, hepatitis C virus, and SARS. Given the rapidity with which new emerging pathogens can appear, it is important to improve animal models that could be used to evaluate vaccination strategies and the protective capacity of different epitopes quickly and reliably. Furthermore, in vivo studies are already required to assess crucial variables of vaccine behavior that are not easily evaluated or impossible to measure in vitro, such as vaccine immunogenicity, vaccine formulation, route of administration, tissue distribution, and involvement of primary and secondary lymphoid organs.

However, few animal models are available for the pathologies which are strictly restricted to humans. In addition, the existing models are expensive, difficult to set up (simian models of HIV infection) or distantly related to the human pathology (mice model of malaria or shigellosis). Because of their simplicity and flexibility, small animals, such as mice represent an attractive alternative to more cumbersome and expensive model systems, such as nonhuman primates, at least for initial vaccine development studies.

Over the last few years, many efforts have been put on the establishment of human/mouse chimera as animal models for "human" diseases including HIV and EBV, and for designing vaccines. Original strategies for creating murine hosts that bear human immune cells involved the adoptive transfer of mature human immune cells into severe combined immunodeficient (scid) recipients; these are referred to as hu-PBL models (Mosier, *Adv Immunol*, 50: 303-325, 1991). Another approach involved the reconstitution of a human immune system in SCID mice through engraftment of human hematopoietic precursor cells; these are referred to as hu-HSC models (McCune, *Curr Opin Immunol*, 3(2): 224-228, 1991). However, those models were limited; the hu-PBL was associated with the graft-versus-host reaction (Garcia et al., *Blood*, 89: 329-336, 1997) and the hu-HSC exhibited poor peripheral T cell reconstitution (Krowka et al., *J Immunol*, 146: 3751-3756, 1991).

After these initial reports in T and B lymphocyte-deficient scid mice (Prkdc$^{scid}$ mutant mice), some level of engraftment was also achieved by transplantation of blood-forming cells in recombination activating gene (RAG)-deficient mice (Rag1$^{-/-}$, Rag2$^{-/-}$ mutant mice; Schultz et al., *J. Immunol.*, 164: 2496-2507, 2000; Goldman et al., *Br. J. Haematol.*, 103: 335-342, 1998). The engraftment levels in these models, however, were still low presumably due to the remaining innate immunity of host animals.

Non-obese diabetic/severe combined immuno-deficient (NOD/scid) mice have been shown to support higher levels of human progenitor cells engraftment than BALB/c/scid or C.B.17/scid mice (Greiner et al, *Stem Cells*, 16: 166-177, 1998). NOD/scid mice harboring either a null allele at the beta-2 microglobulin gene (NOD/scid/β2m$^{-/-}$, Kollet et al, *Blood*, 95: 3102-3105, 2000) or a truncated common cytokine receptor γ chain (γc) mutant lacking its cytoplasmic region (NOD/scid/$\gamma_c^{-/-}$; Ito et al, *Blood*, 100: 3175-3182, 2002) were developed. These mice had deficiencies in T and B cells, like mice deficient in recombination activating gene (RAG$^{-/-}$) or scid mice, but they were also deficient in natural killer (NK) cells due to a deficiency for the common γ chain (γc) of the IL-2 receptor shared by receptors for IL-4, -7, -9, -15, and -21 (reviewed in Macchiarini et al., *J Exp Med*, 202(10): 1307-1311, 2005). HLA-DR1 transgenic NOD/scid mice and HLA-DR3 transgenic Rag2$^{-/-}$ mice were also established (Camacho et al., *Cell Immunol*, 232: 86-95, 2004; WO 2003/018744). However, these models, which were not γc$^{-/-}$, sustain only limited development and maintenance of human lymphoid cells and rarely produce immune responses.

Although engraftment of immunodeficient γc$^{-/-}$ mice with human hematopoietic stem cells leads to the presence of both myeloid and lymphoid lineages, many caveats remain in the original models. In particular, the reproducibility of reconstitution is weak and extremely variable. In addition, poor numbers of T cells are generally recovered in the periphery of the mouse associated to qualitatively and quantitatively altered lymphoid T and B cell responses.

Indeed, weak or no CD4 and CD8 T cell specific effector functions have been reported in response to in vivo immunization or infections, together with weak or no isotype-switch antibody B cell responses due to lack of human T-B cooperation. In order to improve thymic selections and the peripheral survival of T cells, transgenic mice lacking the endogenous MHC molecules (both Class I and Class II) while expressing HLA molecules were constructed in an immunodeficient RAG$^{-/-}$ γc$^{-/-}$ background (WO 2008/010099, WO 2008/010100). However, no engraftment of human hematopoietic cells has ever been obtained with these mice.

In addition, it was observed that only hosts in defined genetic backgrounds, namely BALB/c and NOD (with a superiority of NOD over BALB/c) were permissive to reconstitution by human hematopoietic stem cells (Manz & Di Santo, *Nat Immunol.* 10(10): 1039-1042, 2009; Cachet et al., m/s, 28(1): 6368, 2012; Villaudy, Thèse de l'Ecole Normale Supérieure de Lyon, 2011). Further genetic modifications of the hosts in order to improve reconstitution were thus considerably limited by this situation. Any crossing with non-NOD and non-BALB/c bearing interesting genetic features had to be further backcrossed on one of the "permissive" NOD or BALB/c background to support human hematopoietic engraftment. Similarly, mouse backgrounds usually suitable for transgenesis and to a higher extend homologous recombination did not support human hematopoietic reconstitution. However, the two backgrounds suitable for human hematopoietic reconstitution, NOD and BALB/c, are not convenient for murine genetic engineering, due to poor viability and/or reduced breeding capacity. Consequently, ES cells from F1 litters BALB/c ("permissive") X 129 ("non-permissive") background were used for homologous recombination (see e.g. Strowig et al., *Proc Natl Acad Sci USA*, 108(32): 13218-1323, 2011).

Murine models of numerous human pathologies are available. However, most often, they are restricted to specific genetic backgrounds, as the phenotype mimicking the human disease is only expressed in defined combination of alleles (Linder, *ILAR J.*; 47(2): 132-140, 2006). Thus the restriction of human immune reconstitution to NOD and BALB/c background only is a serious impairment to the analysis in animal models of human diseases and the interaction thereof with the human immune system.

Thus, there is still a need for a convenient animal model enabling efficient, reproducible human hematopoietic reconstitution independently of its genetic background.

DESCRIPTION

The present inventors have now surprisingly found that murine hosts with a non-permissive background could be reconstituted after human progenitor engraftment by the sole expression of the human SIRPα in mice. The reconstituted mice are capable of developing both myeloid and lymphoid human cell lineages from the engraftment of human progenitor cells.

SIRPα (also known as SHPS1, MYD1, or CD172a) is a transmembrane protein containing three Ig-like domains in its extracellular region and putative tyrosine phosphorylation sites in its cytoplasmic region (Matozaki et al., *Trends Cell Biol*, 19: 72-80, 2009; Barclay and Brown, *Nat Rev Immunol*, 6: 457-464). SIRPα is strongly expressed in the brain and in macrophages, dendritic cells, and neutrophils, whereas its ligand CD47 is universally expressed. The SIRPα/CD47 interaction has been shown to be involved in the regulation of macrophage-mediated phagocytosis (Takenaka et al., *Nature Immunol.*, 8(12): 1313-1323, 2007; Ide et al., *Proc. Natl. Acad. Sci. U.S.A.*, 104(12): 5062-5066, 2007; Okazawa et al., *J. Immunol.*, 174(4) 2004-2011, 2005; Legrand et al., *Proc. Natl. Acad. Sci. U.S.A.*, 108(32): 1324-1329, 2011).

Thus, in a first aspect, the invention provides a transgenic mouse, wherein said mouse carries a functional xenogenic SIRPα transgene.

Advantageously, the function of murine T lymphocytes, B lymphocytes and NK cells is abolished in the transgenic mouse of the invention.

Not only does the transgenic mouse of the invention enable reconstitution after human progenitor engraftment, it also displays an additional advantage over NOD/scid mice as being radioresistant. The inventors have indeed observed that the transgenic mice of the invention $Rag^{-/-}$, $\gamma^{-/-}$ xeSIRPα survive at doses as high as 400 rad and display much longer survival than NOD/scid mice (more than 10 month after irradiation and transplantation).

In a first aspect, the present invention provides a transgenic mouse, wherein said mouse has a phenotype comprising:
  a) a deficiency for murine T lymphocytes, B lymphocytes and NK cells,
  b) a deficiency for murine MHC class I and MHC class II molecules, and
  c) a functional xenogenic SIRPα transgene.

Alternatively, the said transgenic mouse is deficient for murine MHC class I and MHC class II molecules.

Preferably, the transgenic mouse of the invention is deficient for T lymphocytes, B lymphocytes and NK cells, and is also deficient for murine MHC class I and MHC class II molecules. Even more preferably, the transgenic mouse of the invention contains a functional xenogenic MHC class I transgene and/or a functional xenogenic MHC class II transgene.

Thus, in a preferred embodiment, the present invention provides a transgenic mouse, wherein said mouse has a phenotype comprising:
  a) a deficiency for murine T lymphocytes, B lymphocytes and NK cells,
  b) a deficiency for murine MHC class I and MHC class II molecules,
  c) a functional xenogenic MHC class I transgene and/or a functional xenogenic MHC class II transgene, and
  d) a functional xenogenic SIRPα transgene.

Among the lymphoid depleted mouse strains, human hematopoietic engraftment is most efficient in the NOD-scid Il2rg$^{null}$ (NSG/NOG) and NOD.Rag1$^{null}$Il2rg$^{null}$ (NOD-RG) strains and it is intermediary in BALB/c.Rag2$^{null}$Il2rg$^{null}$ (BALB-RG) strains. On the other hand, other strains such as e.g. C57BL/6 or 129 strains, with scid, Rag2$^{null}$, Rag2$^{null}$B2m$^{null}$, Rag2$^{null}$Prf$^{null}$, or Rag2$^{null}$Jak3$^{null}$ mutations are unable to reconstitute human hematopoiesis. Remarkably, the present inventors were capable of obtaining long-term hematopoietic engraftment in backgrounds which were previously considered non-permissive for xenotransplantation.

Thus, whereas the prior art taught that only hosts in genetically defined backgrounds such as NOD or BALB/c were permissive to immune reconstitution by human hematopoietic stem cells, the present invention expression of the human SIRPα protein in murine cells enables the engraftment by human hematopoietic progenitors of mice in any background, including previously non-permissive backgrounds. Indeed, the immune reconstitution of such mice by human immune subsets is strictly associated with the expression of SIRPα.

Therefore, in a further preferred embodiment, the present invention provides a transgenic mouse, wherein said mouse is from a non-permissive background, and wherein said mouse has a phenotype comprising:
  a) a deficiency for murine T lymphocytes, B lymphocytes and NK cells,
  b) a deficiency for murine MHC class I and MHC class II molecules,
  c) a functional xenogenic MHC class I transgene and/or a functional xenogenic MHC class II transgene, and
  d) a functional xenogenic SIRPα transgene.

A "background" or a "genetic background" (these terms are used synonymously for the purposes of the present invention), as used herein, is a collection of all genes present in an organism, in particular a mouse, that can influence a trait or traits. As known to the person of skills in the art, each strain has unique background alleles that may interact with and/or modify the expression of a mutation, transgene or other genetic insert (Linder, *ILAR J.;* 47(2): 132-140, 2006; Yohiki and Moriwaki, *ILAR J.;* 47(2): 94-102, 2006; Jackson Laboratory "Genetic Background: understanding its importance in mouse-based biomedical research", A Jackson Laboratory Resource Manual, 2010).

Backgrounds can be either inbred or mixed. An "inbred" background is a genetic background resulting from 20 generations or more of brother-sister mating. As a consequence, every individual in an inbred strain is essentially genetically identical and homozygous at all loci, although minor variations may arise. A list of commonly used inbred strains is provided in table 2 of Linder, *ILAR J.;* 47(2): 132-140, 2006. As used herein, a genetic background which is not inbred is a "mixed" background.

The person of skills in the art will easily realize that each genetic background affords specific advantages, so that it can be used for specific purposes (Linder, *ILAR J.;* 47(2): 132-140, 2006). For example, C57BL/6 is the most widely used inbred strain and the first to have its genome sequenced. Although this strain is refractory to many tumors, it is a permissive background for maximal expression of most mutations. On the other hand, the most widely used ES cells are derived from 129 susbtrains, which show appreciable levels of homologous recombination (in particular, 129/SvJ). The targeted ES cells are then usually injected into C57BL/6 blastocysts to form chimeric mice which are then crossed to C57BL/6 mice: the said mice are good breeders whereas 129 substrains are known to have poor reproduction (Yohiki and Moriwaki, *ILAR J.;* 47(2): 94-102, 2006). Likewise, the FVB/N strain is characterized by a high reproductive capacity, yielding litters of eight or more pups on average. In addition, the FVB/N fertilized eggs contain prominent pronuclei, hence facilitating DNA microinjection therein.

More specifically, NOD and BALB/c backgrounds have been shown to enable reconstitution of the human hematopoiesis system. These two backgrounds are therefore permissive backgrounds. A "permissive background" according to the present invention is a genetic background which enables the xenotransplantation of human hematopoietic stem cells in mouse. By contrast, a genetic background which does not enable the immune reconstitution by human hematopoietic stem cells is herein designated a "non-permissive background". A non-permissive genetic background according to the invention therefore refers to a genetic background where long-term hematopoietic engraftment attempts fail, even when such mutations as scid, Rag2$^{null}$, Rag2$^{null}$B2m$^{null}$, Rag2$^{null}$Prf$^{null}$, or Rag2$^{null}$ Jak3$^{null}$, are introduced into the said background.

Although NOD and BALB/c backgrounds are permissive for human hematopoietic engraftment, they display a number of deleterious features. For example, NOD mice present a high incidence of thymoma, resulting in an abbreviated lifespan. BALB/c mice are poor breeders and are highly radiation-sensitive. These deficiencies make these two backgrounds difficult to use in conventional crosses and/or transgenic experiments.

Advantageously, the non-permissive genetic background can be easily used in murine genetic engineering. Therefore, more preferably, the non-permissive background of the invention is a genetic background which is neither NOD nor BALB/c. Examples of such backgrounds include for example FVB/N, C57BL/6, 129 and C3H, and mixed backgrounds derived thereof.

The expression of a xenogenic SIRPα in the transgenic mouse of the invention improves the efficiency and the reproducibility of the engraftment, whatever the background of the mouse. When heterologous cells (e.g. human peripheral blood mononuclear hematopoietic progenitors) are introduced into the mouse of the present invention, much higher ratios of engraftment and proliferation are observed even in comparison with conventional immunodeficient mice, such as NOD SCID γc$^{-/-}$. In addition, the substitution of the host murine MHC molecules by HLA molecules in the transgenic mouse of the invention impacts both T and B cell functions. In HLA context, the human CD4/MHC class II and CD8/class I interactions increases dramatically the number of T cells both by facilitating positive selection of human thymocytes and peripheral survival of generated human T cells. The haplotype of the murine host should not obligatory the one of the donor cells to ensure the previous functions. If the HLA haplotype is different between the murine hosts and the donor cells, the donor T will be educated in both host and its HLA context. Moreover, HLA expression ensures a strict presentation by the sole HLA molecules. Mice of the invention are used as recipient hosts for human hematopoietic and non-hematopoietic precursors transplantation, to generate new human/mouse multichimera. The skilled person will easily realize that, beyond human hematopoietic and non-hematopoietic precursors, the mice of the invention can generally be used as a universal recipient of any human cell from any origin, including hematopoietic and non-hematopoietic adult cells. For example, transfer of adult peripheral blood lymphocytes could serve as a model of graft-versus-host disease.

Mice deficient for murine MHC and expressing HLA class I and/or class II molecules have been described in the prior art (WO 2008/010099; WO 2008/010100). However, all attempts to engraft these mice with human progenitor cells have failed so far. By contrast, the mice of the invention, which not only are deficient in MHC while producing HLA class I and/or class II molecules, but also express a xenogenic SIRPα protein, can successfully be engrafted by xenogenic progenitor cells. The resulting multichimeric mouse comprises a functional xenogenic (human) immune system restricted to the MHC class I and/or class II molecules (HLA molecules) of the xenogenic species solely.

Thus another advantage of the invention is the permanent reconstitution of the hematopoiesis. The mouse of the invention expresses the full repertoire of xenogenic lymphoid and myeloid cells, including T cells, B cells, NK cells, macrophages and dendritic cells, while maintaining a strong population of xenogenic stem and progenitor cells, as shown in the experimental examples. The invention thus provides animals that express an immune system which is comparable to that of the donor species, especially in respect of the reactive adaptive immune system. In the transgenic mouse of the invention, the xenogenic immune competent cells have a comparable functionality as in the donor body, including a response to antigens and a cytokine profile which is similar to the donor profile. Therefore, the introduction of HLA class I and HLA class II molecules in a murine MHC deficient background in association with the expression of xenogenic SIRPα provides a new immunodeficient mouse which is greatly improved over conventional humanized mice, both quantitatively, through induction of higher levels of human immune cells, and qualitatively, by increasing reproducibility and promoting efficient and human HLA-restricted immune responses.

It is also noteworthy that such a mouse is very easy to obtain, since it only requires transgenesis by human Sirpa. In particular, no fastidious, complicated backcrossing is required (Strowig et al., *Proc Natl Acad Sci USA*, 108(32): 13218-1323, 2011; Schroeder and DiPersio, *Dis Model Mech*, 4(3): 318-33, 2011).

The term "transgenic mouse" as used herein refers to a mouse that contains within its genome at least one specific gene that has been disrupted or otherwise modified or mutated by the methods described herein or methods otherwise well known in the art.

A "xenogenic" protein as used herein is a protein which is from a different species than the host animal in which it is expressed. Thus, the xenogenic SIRPα of the invention is a protein originating from a species different from *Mus musculus*. Preferably, the SIRPα protein of the invention is the human SIRPα. Most preferably, human SIRPα has the amino acid sequence represented by SEQ ID NO. 1, and/or is encoded by a polynucleotide having the nucleotide sequence represented by SEQ ID NO. 2.

As used herein, the term "transgene" refers to a nucleic acid sequence that is partly or entirely heterologous, i.e., foreign, to the transgenic animal into which it is introduced, or is homologous to an endogenous gene of the transgenic animal into which it is introduced, but which is designed to be inserted, or is inserted, into the animal's genome in such a way as to alter the genome of the cell into which it is inserted (e.g., it is inserted at a location that differs from that of the natural gene). A "functional transgene" is one that produces an mRNA transcript, which in turn produces a properly processed protein in at least one cell of the mouse comprising the transgene. One of skills in the art will realize that a functional transgene can be operably linked to one or more transcriptional regulatory sequences and any other nucleic acid, such as introns, that may be necessary for optimal expression of a selected nucleic acid.

A nucleic acid, such as the said transgene, is "operably linked" when it is placed into a functional relationship with another nucleic acid sequence. Such sequences include both expression control sequences that are contiguous with the said transgene of interest and expression control sequences that act in trans or at a distance to control the transgene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e. Kozak consensus sequence); sequences that enhance protein stability; and when desired, sequences that enhance protein secretion.

In an embodiment of the invention, the gene encoding human SIRPα is under the control of a promoter enabling expression in murine cells. Advantageously, the said promoter is a promoter which confers specific expression in macrophages, dendritic cells, and/or neutrophils. Preferably, the said promoter confers specific expression in macrophages. Promoters enabling specific macrophage expression are well known in the art (see e.g. Clarke and Gordon, *J Leukoc Biol*, 63(2):153-168, 1998; Tenen et al., *Blood*, 90: 489, 1997). Such promoters include for example the sheep visna virus long terminal repeat (Bellosta et al., *J. Clin. Invest*, 96: 2170-2179, 1995), the macrosialin (CD68) promoter (Li et al., *J. Biol. Chem.*, 273: 5389-5399, 1998), the chicken lysozyme promoter (Whitman et al., *J. Lipid Res*, 43: 1201-1208, 2002), the scavenger receptor-A (SA) promoter (Horvai et al., *Proc. Natl. Acad. Sci. U.S.A*, 92: 5391-5395, 1995), and the c-fms proto-oncogene promoter (Carninci et al., *Nat Genet*, 38: 626-635, 2006; Gross and Oelgeschlager, *Biochem. Soc. Symp*, 73: 225-236, 2006). Preferably, the promoter according to the invention is the c-fms promoter.

"HLA" is the human MHC complex, and "H-2" the mouse MHC complex. The MHC class I molecule comprises an α-chain (heavy chain) which is non-covalently associated with a β2-microglobulin (β2-m) light chain. The MHC class II molecules are heterodimers comprising an α-chain and a β-chain. The human complex comprises three class I σ-chain genes, HLA-A, HLA-B, and HLA-C, and three pairs of MHC class II α- and β-chain genes, HLA-DR, -DP, and -DQ. In many haplotypes, the HLA-DR cluster contains an extra β-chain gene whose product can pair with the DRα chain, and so the three sets of genes give rise to four types of MHC class II molecules. In the mouse, the three class I α-chain genes are H-2-L, H-2-D, and H-2-K. The mouse MHC class II genes are H-2-A and H-2-E. H-2-Eα is a pseudogene in the H2$^b$ haplotype.

In another embodiment, the invention provides a transgenic mouse wherein the deficiency in murine MHC class I molecules is associated with a deficient β2-microglobulin gene, preferably a disrupted β2-microglobulin gene ($β_2m^{-/-}$, $β_2m$ knock-out); the absence of β2-microglobulin chain in the mouse leads to lack of murine MHC class I molecules (H-2-L, H-2-D, and H-2K) cell surface expression.

In a preferred embodiment, the β2-microglobulin gene and at least one of the class I α-chain genes, for example the H2-D$^b$ and/or H2-K$^b$ genes, are disrupted.

$β_2m$ knock-out mice are well-known to those of ordinary skill in the art. For example, $β_2m^{-/-}$ mice are described in Zijlstar et al (*Nature*, 344: 742-746, 1990), and $β_2m^{-/-}$, H2-D$^b$ and/or H2-K$^b$ mice can be obtained as described in Pascolo et al (*J. Exp. Med.*, 185: 2043-2051, 1997).

In another embodiment, the invention provides a transgenic mouse wherein the deficiency in murine MHC class II molecules is associated with a deficient H-2$^b$-Aβ gene, and eventually a deficient H-2-Eβ gene.

In a H2$^b$ haplotype, the deficiency in murine MHC class II molecules is obtained by disrupting the H-2$^b$-Aβ gene (I-Aβ$^b$ knock-out or I-Aβ$^b$ $^{-/-}$); the absence of H-2 I-Aβ-chain leads to lack of conventional H-2 I-A and I-E class II molecules cell surface expression, since H-2-Eα is a pseudogene in this haplotype. In the other H-2 haplotypes, the deficiency in murine MHC class II molecules is obtained by disrupting both H-2-Aβ and H-2-Eβ genes.

I-Aβ$^b$ knock-out mice are well-known to those of ordinary skill in the art. For example, I-Aβ$^b$ $^{-/-}$ mice are described in Takeda et al, Immunity, 1996, 5, 217-228. Mice knocked out for both H-2-Aβ and H-2-Eβ genes are described in Madsen et al (*Proc. Natl. Acad. Sci. USA*, 96: 10338-10343, 1999).

One of the difficulties hampering the design of T-epitope-based vaccines targeting T lymphocytes is HLA class I/class II molecule polymorphism. It is known in the art that genetic diversity exists between the HLA genes of different individuals as a result of both polymorphic HLA antigens and distinct HLA alleles Due to the high degree of polymorphism of the HLA molecules, the set of epitopes from an antigen, which are presented by two individuals may be different depending on the HLA molecules or HLA type which characterize said individuals. However, despite of a high number of HLA molecules whose repartition is not homogeneous worldwide, some alleles are predominant in human populations (HLA-DR1, -DR3, -B7, -B8, -A1, -A2). For example, HLA-A2.1 and HLA-DR1 molecules are expressed by 30 to 50% and 6 to 18% of individuals, respectively. In addition, there is a redundancy of the presented set of peptides between HLA class I isotypic or allelic variants and the binding of peptides to HLA class II molecules is less restrictive than to class I molecules. Therefore, the peptides which are presented by the HLA-A2.1 and HLA-DR1 molecules should be representative of the epitopes that are presented by most individuals of the population. Nevertheless, it may be desirable to identify the optimal epitopes that are presented by other HLA isotypic or allelic variants, to cover the overall human population. This may be also important in cases where there is a bias in the immune response, so that the antigen is preferably presented by other HLA haplotypes. This may be also relevant in cases where the HLA haplotypes are involved in disease development or outcome, for example auto-immune diseases (Jones et al, *Nature Rev Immunol*, 6: 271-282, 2006,) or viral infections like HCV (Yee, *Genes Immun*, 5: 237-245, 2004) or HIV (Bontrop and Watkins, *Trends Immunol*, 26: 227-233, 2005).

The transgenic mouse of the present invention may comprise one or more functional xenogenic MHC class I and/or class II transgene(s). Preferably the allotypes of the MHC class I and/or class II transgenes are reflective of the genetic variability of the xenogenic population. For example, the allotypes which are the most frequent in the xenogenic population are chosen so as to cover the overall xenogenic population. The xenogenic MHC class I and/or class II transgenes may have the sequence of the alleles that are present in the precursor cells or the sequence of other alleles that are not present in the precursor cells.

Preferably, the xenogenic MHC class I transgene and xenogenic MHC class II transgene are from the same species as the xenogenic SIRPα transgene. More preferably, all these transgenes are human, i.e. the xenogenic MHC class I transgene is a human HLA class I transgene, xenogenic MHC class II transgene is a human HLA class II transgene, and the xenogenic SIRPα transgene is a human gene.

The human HLA class I and class II transgenes may have the sequence of the alleles that are present in the precursor cells or the sequence of other alleles that are not present in the precursor cells.

Preferably, the human HLA class I and class II transgenes correspond to allotypes that are the most frequent in the human population.

For example, the human HLA class I transgene is an HLA-A2 transgene and the HLA class II transgene is an HLA-DR1 transgene.

More preferably, the HLA-A2 transgene encodes a HLA-A2.1 mono-chain in which the human β2m is covalently linked by a peptidic arm to the HLA-A2.1 heavy chain.

The HLA-DR1α and β chains may be encoded by the HLA-DRA*0101 and the HLA-DRB 1 *0101 genes, respectively.

HLA class I and HLA class II transgenic mice are well-known to those of ordinary skill in the art. For example, HLA-A2.1 transgenic mice expressing a chimeric mono-chain (α1-α2 domains of HLA-A2.1 (encoded by HLA-A*0201 gene), α3 to cytoplasmic domains of H-2 $D^b$, linked at its N-terminus to the C terminus of human β2m by a 15 amino-acid peptide linker) are described in Pascolo et al (*J. Exp. Med*, 185: 2043-2051, 1997).

HLA-DR1 transgenic mice expressing the DR1 molecule encoded by the HLA-DRA*0101 and HLA-DRB 1 *0101 genes are described in Altmann et al, J. Exp. Med., 1995, 181, 867-875.

Accordingly, embodiments of the invention disclosed herein may substitute one polymorphic HLA antigen for another or one HLA allele for another.

It is known in the art that genetic diversity exists between the HLA genes of different individuals as a result of both polymorphic HLA antigens and distinct HLA alleles. Accordingly, embodiments of the invention disclosed herein may substitute one polymorphic HLA antigen for another or one HLA allele for another. Examples of HLA polymorphisms and alleles can be found, for example, in the IMGT/HLA Database (http://www.ebi.ac.uk/imgt/hla) and in Genetic diversity of HLA: Functional and Medical Implication, Dominique Charon (Ed.), EDK Medical and Scientific International Publisher, and The HLA FactsBook, Steven G. E. Marsh, Peter Parham and Linda Barber, AP Academic Press, 2000. The IMGT/HLA Database provides a database for sequences of the human major histocompatibility complex (HLA) and includes the official sequences for the WHO Nomenclature Committee For Factors of the HLA System.

A "deficiency" according to the invention refers to the lack of a molecular or cellular function. Therefore, a mouse displaying a deficiency for murine T lymphocytes, B lymphocytes and NK cells is a mouse which shows no detectable functional murine T lymphocytes, B lymphocytes and NK cells. This absence of functional murine T lymphocytes, B lymphocytes and NK cells will for example result from the presence of inactivating mutations in one or more genes essential for the development of T, B and/or NK cells. A "mutation" as used herein refers to the substitution, insertion, deletion of one or more nucleotides in a polynucleotide sequence. An inactivating mutation results in a product which function is either reduced or abolished. In particular, an inactivating mutation may be a spontaneous mutations or a targeted mutation, i.e. a mutation resulting in disrupted gene.

Preferably, the mouse displaying a deficiency for murine T lymphocytes, B lymphocytes and NK cells according to the invention carries at least two such mutations. Mutations affecting genes essential for the development of T, B and/or NK cells are well known in the art. Combinations of these mutations include for example include, for example: a first mutation which is the mouse scid mutation ($Prkdc^{scid}$; Bosma et al, *Nature,* 301: 527-530, 1983; Bosma et al, *Curr. Top. Microbiol., Immunol.,* 137: 197-202, 1988) or the disruption of the recombination activating gene ($Rag1^{-/-}$ or $Rag2^{-/-}$; Mombaerts et al, *Cell,* 68: 869-877, 1992; Takeda et al, *Immunity,* 5: 217-228, 1996), and a second mutation which is the beige mutation ($Lyst^{bg}$; Mac Dougall et al, *Cell. Immunol.,* 130: 106-117, 1990) or the disruption of the $β_2$-microglobulin gene ($β_2m^{-/-}$; Kollet et al, *Blood,* 95: 3102-3105, 2000), the IL-2 receptor γ chain (or common cytokine receptor γ chain ($γ_c$)) gene (IL-2R$γ^{-/-}$ or $γ_c^{-/-}$; DiSanto et al, *Proc Natl Acad. Sci.,* 92: 377-381, 1995), or the IL-2 receptor β chain (IL-2Rβ) gene (IL-2R$β^{-/-}$; Suzuki et al; *J. Exp. Med.,* 185: 499-505, 1997).

More preferably, the transgenic mouse of the invention has a genotype selected from the group consisting of:

$Rag2^{-/-}$, $γ_c^{-/-}$, $β_2m^{-/-}$, I-A$β^{b-/-}$, xeSIRPα

$Rag2^{-/-}$, $γ_c^{-/-}$, $β_2m^{-/-}$, I-A$β^{b-/-}$, HLA-A2$^{+/+}$, HLA-DR1$^{+/+}$, xeSIRPα

$Rag2^{-/-}$, $γ_c^{-/-}$, $β_2m^{-/-}$, I-A$β^{b-/-}$, HLA-A2$^{+/+}$, xeSIRPα, and $Rag2^{-/-}$, $γ_c^{-/-}$, $β_2m^{-/-}$, I-A$β^{b-/-}$, HLA-DR1$^{+/+}$, xeSIRPα.

Still more preferably, the transgenic mouse of the invention has the genotype $Rag2^{-/-}$, $γ_c^{-/-}$, $β2 m^{-/-}$, I-A$β^{b-/-}$, HLA-A2$^{+/+}$, HLA-DR1$^{+/+}$, xeSIRPα.

This embodiment is particularly advantageous since the mouse of the invention does not express any MHC molecule anymore whereas it expresses both class I and class II HLA molecules on thymic epithelial cells. By contrast, the humanized mice of the art either do not express HLA molecules or express only HLA-A2 (Schultz et al., *Nat Rev Immunol.* 7(2): 118-130, 2007; Takenaka et al., *Nature Immunol.,* 8(12): 1313-1323, 2007; Strowig et al., *Proc Natl Acad Sci USA,* 108(32): 13218-1323, 2011; Legrand et al., *Proc. Natl. Acad. Sci. U.S.A.,* 108(32): 1324-1329, 2011).

Thus, in this specific mouse of the invention, not only are the T cells educated by the sole human HLA molecules, but in addition they benefit from the presence of both class I and class II molecules. Stronger interactions between the MHC and TCR/CD4/CD8 are observed, which lead to higher thymic selection and higher peripheral survival than in the mice of the prior art. As a consequence, and as shown in the experimental examples, the mouse of the invention expresses both CD4$^+$ and CD8$^+$ T cells, leading to a fully human immune response.

Most preferably, the xenogenic SIRPα is human.

In a preferred embodiment, the transgenic mouse of the invention is also deficient for the complement. Even more preferably, the transgenic mouse of the invention is deficient for the C5 protein of the complement.

A "disrupted" gene is one that has been mutated using homologous recombination or other approaches known in the art. A disrupted gene can be either a hypomorphic allele of the gene or a null allele of the gene. One of skill in the art will recognize that the type of allele to be used can be selected for any particular context. In many embodiments of the invention, a null allele is preferred.

The term "homologous recombination" refers to the exchange of DNA fragments between two DNA molecules or chromatids at the site of homologous nucleotide sequences. Homologous recombination has been widely used in the art for targeting mutations to a preselected, desired gene sequence of a cell in order to produce a transgenic animal (Mansour et al., Nature 336: 348-352, 1988; Capecchi, Trends Genet, 5: 70-76, 1989; Capecchi, Science, 244: 1288-1292, 1989; Frohman, Cell, 56: 145-147, 1989). Detailed methodologies for homologous recombination in mice are available and it is now be feasible to deliberately alter any gene in a mouse (Capecchi, Trends Genet, 5: 70-76, 1989; Frohman et al., Cell, 56: 145-147, 1989). Gene targeting involves the use of standard recombinant DNA techniques to introduce a desired mutation into a cloned DNA sequence of a chosen locus. That mutation is then transferred through homologous recombination to the genome of a pluripotent, embryo-derived stem (ES) cell. The altered stem cells are microinjected into mouse blastocysts and are incorporated into the developing mouse embryo to ultimately develop into chimeric animals. In some cases, germ line cells of the chimeric animals will be derived from the genetically altered ES cells, and the mutant genotypes can be transmitted through breeding.

The chimeric or transgenic animal cells of the present invention are prepared by introducing one or more DNA molecules into a cell, which may be a precursor pluripotent cell, such as an ES cell, or equivalent (Robertson, In: Current Communications in Molecular Biology, pp. 39-44, Capecchi (ed.), Cold Spring Harbor Press, Cold Spring Harbor, N.Y., 1989). The pluripotent (precursor or transfected) cell can be cultured in vivo in a manner known in the art (Evans et al., Nature, 292: 154-156, 1981) to form a chimeric or transgenic animal. Any ES cell can be used in accordance with the present invention. It is, however, preferred to use primary isolates of ES cells. Such isolates can be obtained directly from embryos, such as the CCE cell line disclosed by Robertson (In: Current Communications in Molecular Biology, pp. 39-44, Capecchi (ed.), Cold Spring Harbor Press, Cold Spring Harbor, N.Y., 1989). Preferably, the ES cell of the invention is obtained from an embryo of a 129 substrain. Alternatively, they can be obtained from the clonal isolation of ES cells from the CCE cell line (Schwartzberg et al., Science, 246: 799-803, 1989, which reference is incorporated herein by reference). Such clonal isolation can be accomplished according to the method of Robertson (In: Teratocarcinomas and Embryonic Stem Cells: A Practical Approach, Robertson (Ed.), IRL Press, Oxford, 1987), which reference and method are incorporated herein by reference. The purpose of such clonal propagation is to obtain ES cells, which have a greater efficiency for differentiating into an animal. Clonally selected ES cells are approximately 10-fold more effective in producing transgenic animals than the progenitor cell line CCE. For the purposes of the recombination methods of the present invention, clonal selection provides no advantage.

In addition, it is also possible to derive induced pluripotent cells by the "dedifferentiation" of fibroblasts or other differentiated cells from embryos or adults by the enforced expression of nuclear reprogramming factors. Preferably, the said reprogramming factor will include Oct4 and Sox2 (Takahashi et al., Cell, 131(5): 861-872, 2007), although other reprogramming factors are known in the art (see e.g. U.S. Pat. No. 8,058,065 which mentions a combination of genes encoding Oct3/4, Klf4, c-Myc and Sox2).

An example of ES cell lines, which have been clonally derived from embryos, are the ES cell lines, AB1 (hprt$^+$) or AB2.1 (hprt$^-$). The ES cells are preferably cultured on stromal cells (such as STO cells (especially SNC4 STO cells) and/or primary embryonic fibroblast cells) as described by Robertson (In: Teratocarcinomas and Embryonic Stem Cells: A Practical Approach, pp 71-112, Robertson (Ed.), IRL Press, Oxford, 1987), which reference is incorporated herein by reference. Methods for the production and analysis of chimeric mice are disclosed by Bradley (In: Teratocarcinomas and Embryonic Stem Cells: A Practical Approach, pp 113-151, Robertson (Ed.), IRL Press, Oxford, 1987), which reference is incorporated herein by reference. The stromal (and/or fibroblast) cells serve to eliminate the clonal overgrowth of abnormal ES cells. Most preferably, the cells are cultured in the presence of leukocyte inhibitory factor ("lif") (Gough et al., Reprod. Fertil. Dev., 1: 281-288, 1989; Yamamori et al., Science, 246: 1412-1416, 1989, both of which references are incorporated herein by reference). Since the gene encoding lif has been cloned (Gough et al., Reprod. Fertil. Dev., 1: 281-288, 1989), it is especially preferred to transform stromal cells with this gene, by means known in the art, and to then culture the ES cells on transformed stromal cells that secrete lif into the culture medium.

In another aspect, the present invention provides a method for producing a multichimeric mouse, said method comprising the step of transplanting, by any appropriate means, precursor cells of a xenogenic species into the transgenic mouse of the invention, wherein the precursor cells comprise hematopoietic and non-hematopoietic precursors.

In yet another aspect, the present invention provides a method for producing a multichimeric mouse, said method comprising the step of transplanting, by any appropriate means, adult cells of a xenogenic species into the transgenic mouse of the invention, wherein the precursor cells comprise hematopoietic and non-hematopoietic adult cells.

The method of the invention enables the provision of chimeras of equal value and provides thus a reduction of the high interindividual variability known in the prior art. Thus it is also an object of the invention to provide a multichimeric mouse obtained by the said method. Preferably, the said mouse is from a non-permissive background.

Advantageously, the grafted precursor cells originate from the same species as the xenogenic SIRPα transgene. More advantageously, the grafted precursor cells are from the said species as the functional MHC class I transgene and the functional MHC class II transgene and the functional xenogenic SIRPα transgene. Preferably, the grafted precursor cells are human precursor cells.

A "stem cell", as used herein, refers to a pluripotent or multipotent cell having clonogenic and self-renewing capabilities and the potential to differentiate into multiple cell lineages. These cells allow the reconstitution of multiple somatic tissue types. More specifically, a "hematopoietic stem cell" is a cell that can proliferate and can generate all cells of the hematopoietic system, in particular the immune system. A "precursor" or a "precursor cell" according to the invention is a committed cell having the potential to differentiate into a particular cell lineage. These cells allow the reconstitution of a specific somatic tissue type. A "hematopoietic precursor" according to the invention is thus a precursor cell which is engaged into hematopoiesis and which differentiates within a particular cell lineage. The hematopoietic lineage cell resulting from the differentiation may be, for example, a B-cell, T-cell, dendritic cell, monocyte, neutrophil, macrophage, natural killer cell, granulocyte, erythrocyte, eosinophil, megakaryocyte, platelet, bone marrow, splenic, dermal, or stromal cell.

According to the method of the present invention, the hematopoietic precursors and non-hematopoietic precursors may be from a single donor; in this case the precursors have the same genotype (syngenic precursors). Alternatively, the precursors (hematopoietic precursors and/or non-hematopoietic precursors) may be from two or more donors; in this case the precursors (hematopoietic precursors and/or non-hematopoietic precursors) consist in cells whose genotype (including MHC haplotype) is different.

According to the method of the present invention, the hematopoietic precursors and non-hematopoietic precursors may be isolated from appropriate tissues (fetal tissue, cord-blood, adult bone-marrow) or they may be derived in vitro, from adult or embryonic stem cells, by methods which are well-known to those of ordinary skill in the art. For example, methods for differentiating human embryonic stem cells in multiple different lineages, in vitro, are described in Hyslop et al, *Expert. Rev. Mol. Med.,* 7: 1-21, 2005; Odorico et al, *Stem Cells,* 19: 193-204, 2001. Methods for differentiating human embryonic stem cells, specifically in $CD34^+$ cells, hepatic cells, pancreatic cells or neurons are described, respectively, in: Vodyanik et al, *Blood,* 105: 617-626, 2005; Lavon et al, *Differentiation,* 72: 230-238, 2004 and Levon and Benvenisty, *J. Cell. Bloch.,* 96:1193-1202, 2005; Assady et al, *Diabetes,* 50: 1961-1967, 2001; Zhang et al, *Nat. Biotechnol.,* 19: 1129-1 133, 2001. For example, methods for differentiating human adult stem cells in multiple different or single lineages, in vitro, are reviewed in Körbling et al., *N Engl J Med,* 349: 570-582, 2003.

In a first embodiment, the invention provides a method wherein the precursor cells are derived from stem cells.

The use of stem cells allows deriving more progenitor cells since the source of biological material is available in higher quantity and contains more precursor cells, in particular for the $CD34^+$ hematopoietic precursors. In addition, the embryonic stem cells are less immunogenic. These advantages increase the reproducibility between different mouse chimera obtained by transplantation of the same progenitor cells preparation to different mice of the same transgenic strain.

In another embodiment, the invention provides a method wherein the precursor cells are human precursor cells.

In another embodiment, the invention provides a method wherein the hematopoietic precursor cells are human $CD34^+$ cells.

In another embodiment, the invention provides a method wherein the non-hematopoietic precursor cells are selected from the group consisting of: hepatocyte, neuron, adipocyte, myocyte, chondrocyte, or melanocyte precursors, and endothelial, glial, or pancreatic cells precursors.

In another embodiment, the invention provides a method wherein the hematopoietic precursors or non-hematopoietic precursors are genetically modified by an oligonucleotide or a polynucleotide of interest, so as to induce the expression of a heterologous gene or inhibit the expression of an endogenous gene. The modification may be stable or transient. For example, the cells may be transgenic cells expressing a gene of interest, such as a cytokine gene or an oncogene. For example the transgenic expression of IL-7 or IL-15 involved in the generation/maintenance of T cell memory may be useful to induce efficient vaccination. Precursor cells may be transgenic for the expression of human c-Ha-ras gene with its own promoter which promotes further induction of carcinoma after treatment by genotoxic carcinogens like N-ethyl-N-nitrosourea, 7,12-dimethylbenz(a)anthracene (DMBA) or urethane (Okamura et al., Cancer Let, 245(1-2): 321-330, 2007). The conditional expression of oncogenes like SV40 early sequence under the control of the regulatory sequences of the human antithrombin III gene that confer hepatic expression, may provide good model for hepatic carcinomas (Lou et al., *Cancer Let,* 229: 107-114, 2005). Alternatively, the cells may be transiently modified by a siRNA targeting a gene of interest for example conditional shutting down of the expression of IL-2 gene involved in regulatory T cells maintenance/function may be advantageous for the development of efficient vaccination. The conditional knocking down of pro-apoptotic genes may also be investigated for the occurrence of tumors.

The hematopoietic progenitor cells may advantageously comprise a genetic modification that improves the differentiation of hematopoietic precursors into functional T, B and dendritic cells. These modifications are well-known to those skilled in the art. For example, conditional expression of STAT5 in the hematopoietic precursor cells may be obtained as described in Kyba and Daley (*Exp Hematol,* 31(11): 994-1006, 2003).

In another embodiment, the invention provides a method wherein the hematopoietic precursors and non-hematopoietic precursors are from donors of different MHC haplotypes, more preferably of the haplotypes that are the most frequent in the xenogenic species, to take into account the xenogenic MHC polymorphism. For example, the mice are transgenic for the HLA haplotypes that are the most frequent in the human population. These humanized mice have HLA molecules that are reflective of the genetic variability of the human population. Therefore, their immune system is reflective of the immune system of most individuals of the population.

The haplotype of the precursor cells may also correspond to an haplotype that is involved in disease development or outcome, for example autoimmune diseases (Jones et al, *Nature Rev Immunol.,* 6: 271-282, 2006) or viral infections like HCV (Yee, *Genes Immun,* 5: 237-245, 2004) or HIV (Bontrop and Watkins, *Trends Immunol.,* 26: 227-233, 2005).

In another embodiment, the invention provides a method wherein the hematopoietic precursors and non-hematopoietic precursors are transplanted simultaneously.

In another embodiment, the invention provides a method wherein the hematopoietic precursors and non-hematopoietic precursors are transplanted sequentially.

In another embodiment, the invention provides a method wherein the hematopoietic precursors and non-hematopoietic precursors are transplanted in the same site of the mouse.

In another embodiment, the invention provides a method wherein the hematopoietic precursors and non-hematopoietic precursors are transplanted in a different site of the mouse.

Methods of transplanting progenitor cells into mice are well-known in the art. In general, the transgenic mice in which chimerism is to be generated, are made more receptive by conditioning that inter alia is aimed at removal of residual murine immune-competent cells for a subsequent transplantation of xenogenic precursor cells. Preferably, this is done by radioactive irradiation of the recipient animal at a sublethal dose. For example, the sublethal dose for a single irradiation for NOD/SCID mice is in general 200-250 cGy. The hematopoietic progenitor cells are preferably transplanted into a sublethaly irradiated newborn mice. The cells, derived from fetal-tissue, bone-marrow, cord-blood or embryonic stem cell, may be cultured for an appropriate time before transplantation, to improve the engraftment rate of the hematopoietic progenitors into the transgenic mouse.

The number of cells that are transplanted is determined so as to obtain optimal engraftment into the transgenic mouse. For example, from $10^4$ to $10^6$ human CD34$^+$ cells are transplanted intraperitoneally, intra-hepatically, or intravenously, for example via a facial vein, into sublethally irradiated newborn transgenic mice, as described in Traggiai et al, *Science*, 304: 104-107, 2004; Ishikawa et al, *Blood*, 106: 1565-1573, 2005; Gimeno et al, *Blood*, 104: 3886-3893, 2004.

The hematopoietic and non-hematopoietic progenitor cells may be transplanted simultaneously or sequentially. Both strategies may be dictated both by scientific or technical reasons. For example, it may be difficult to inject the same day neuronal and hematopoietic precursors into brain and liver of newborn mice, while hepatic and hematopoietic precursors can be injected simultaneously in the liver. Preferably, the transplantation of the hematopoietic tissue is intrahepatic and the transplantation of the non-hematopoietic tissue is orthotopic or not depending on the organ. For example, the hematopoietic/hepatic reconstitution are achieved by transplantating both precursors intrahepatically. The hematopoietic/neuronal reconstitutions are achieved by transplanting the hematopoietic precursors intra-hepatically and the non-hematopoietic precursors at the orthotopic site (brain). The hematopoietic/pancreatic reconstitutions are achieved by transplanting the hematopoietic precursors intrahepatically and the pancreatic precursors under the kidney capsules of the murine hosts.

Advantageously, the non-hematopoietic progenitor cells are not only maintained in the transgenic mice of the invention after transplantation, but are also capable of growing. The capacity of the non-hematopoietic progenitor cells "to maintain" as used herein refers to the capacity for these progenitor cells to survive in the host. The capacity of implanted progenitor cells "to grow" as used herein refers to the capacity of settled progenitor cells, not only to survive in the recipient but also to multiply in the obtained chimeric model. Growth can be measured by quantitative imaging and evaluating the percentage of cells expressing a specific cell type marker. Measurements can be made at different time points to follow the repopulation of the settled progenitor cells.

More advantageously, the progenitor cells are capable of differentiating into a specific tissue. The capacity of progenitor cells "to differentiate" as used herein refers to progenitor cells having the capacity to reach, after the implanting step, characteristics as similar as possible to those in their original host, e.g., in humans. This capacity can be determined in terms of secreted molecules (such as h$\alpha$1AT for the hepatocytes), expressed surface receptors, pathogen infection, cell size or any other appropriate methods. The presence of xenogenic cell type-specific molecules expressed by the xenogenic cells can be measured, on murine sera, by well-known techniques such as ELISA (enzyme-linked immunosorbent assay), Western Blot, dot blot, immunoprecipitation, direct or indirect immunostaining on histological sections using specific antibodies of implanted cell markers. The cell type-specific molecule transcripts can be detected by RT-PCR (reverse transcriptase-polymerase chain reaction) or real-time RT-PCR by using specific primers of implanted cell markers. Specific receptors can be detected by various techniques such as FACS analysis.

An advantage of the multichimeric mouse of the invention is not only the maintenance of the settled progenitor cells, but also their growth and differentiation. In particular, the multichimeric mouse of the invention is capable of developing all myeloid and lymphoid human cell lineages from the engraftment of human progenitor cells.

The multichimeric mouse of the invention is capable of developing a human HLA-restricted CD8 specific T cell response upon vaccination. The multichimeric mouse of the invention is thus useful for analyzing the specific human immune response to infections and the immunopathogenesis of human infections. In addition, the multichimeric mouse of the invention is particularly useful for assaying the efficiency and the safety of vaccine candidates.

The multichimeric mouse of the invention can advantageously be utilized as a platform technology for the further development of models for infectious diseases (such as HSV, EBV, HIV, rubella), autoimmune diseases, tumorous diseases, transplantation-associated diseases or inflammatory diseases and therapeutic strategies, as well as the role of the immune system in tissue differentiation in vivo. For example, the mouse of the invention is perfectly suited for the development of models for testing the teratogenicity of stem cells dedicated to regeneration medicine or the tumorogenicity in cell therapy. It will also be apparent to the person of skills in the art that the mouse of the invention can be a very useful model for studying human pathogens, as well as for screening compounds active against the said pathogens. The mouse of the invention provides a model useful in the development and optimization of vaccines or immunotherapies in vivo for human use.

In a preferred embodiment of the preceding uses, the multichimeric mouse comprises:
  a functional SIRP$\alpha$ protein of the xenogenic species,
  functional transgenic-MHC class I and/or MHC class II molecules of the xenogenic species; the MHC class I and class II molecules may correspond to an haplotype which is identical or different to that of the transplanted precursor cells,
  a functional immune system of the xenogenic species, which is restricted to the transgenic MHC class I and/or MHC class II molecules solely,
  a functional tissue of the xenogenic species,
  a lack of functional murine T lymphocytes, B lymphocytes and NK cells, and
  a lack of murine MHC class I and MHC class II molecules cell surface expression.

In a further preferred embodiment of the preceding uses, the said mouse is from a non-permissive background.

In a still further preferred embodiment, the tissue is selected from the group consisting of: hepatic, nervous, adipose, cardiac, chondrocytic, endothelial, pancreatic, muscle and skin tissues.

The invention relates also to a method of studying the immuno-pathogenesis of a tissue-specific disease, in vivo, the said method comprising the steps of:
  a) inducing a pathology in the tissue of the multichimeric mouse as defined above, and
  b) analyzing the immune response to the pathological tissue, into the multichimeric mouse, by any appropriate means.

According to a preferred embodiment of said method, step a) is performed by inoculating a pathogenic microorganism to the mouse chimera, by any appropriate means.

Pathogenic microorganisms include with no limitation: bacteria, fungi, viruses, parasites and prions. Bacteria include for example: *C. diphtheriae, B. pertussis, C. tetani, Haemophilus influenzae, S. pneumoniae, Escherichia coli, Klebsiella, Streptococcus aureus, S. epidermidis, Neisseria meningiditis, Bacillus anthracis, Listeria, Chlamydia trachomatis, Chlamydia pneumoniae, Rickettsiae*, Group A

*Streptococcus*, Group B *Streptococcus*, *Pseudomonas aeruginosa*, *Salmonella*, *Shigella*, *Mycobacteria* (e.g. *Mycobacterium tuberculosis*) and *Mycoplasma*. Viruses include for example: Polio, Mumps, Measles, Rubella, Rabies, Ebola, Hepatitis A, B, C, D and E, Varicella Zoster, Herpes simplex types 1 and 2, Parainfluenzae, types 1, 2 and 3 viruses, Human Immunodeficiency Virus I and II, RSV, CMV, EBV, Rhinovirus, Influenzae virus A and B, Adenovirus, Coronavirus, Rotavirus and Enterovirus. Fungi include for example: *Candida* sp. (*Candida albicans*) and filamentous fungi such as *Aspergillus fumigatus*. Parasites include for example: *Plasmodium* (*Plasmodium falciparum*), *Pneumocystis carinii*, *Leishmania*, and *Toxoplasma*.

According to another preferred embodiment of said method, step a) is performed by inoculating an inductor of a tumor or an auto-immune disease to the mouse chimera, by any means.

Inductors of tumors or auto-immune diseases are well-known to those of ordinary skill in the art. For example, streptozotocine may be used to induce autoimmune diabetes, and DSS (Dextran sulfate sodium) may be used to induce Inflammatory Bowel Disease (IBD; Shintani et al, *Gen Pharmacol*, 31: 477-488, 1998). Urethane may also be used to induce lung adenocarcinoma (Steraman et al, *Am. J. Pathol.*, 167: 1763-1775, 2005).

According to another preferred embodiment of said method, step b) comprises assaying for the presence of a humoral response, a T-helper cell response or a T-cytotoxic cell response to an antigen which is expressed in said pathological tissue.

The presence of an immune response to the antigen is assayed by any technique well-known in the art.

The presence of a humoral response to the antigen is assayed by measuring, either the titer of antigen-specific antibodies from the sera of murine hosts, by ELISA, or the number of antibody secreting cells, by ELISPOT.

The presence of a T-helper cell response to the antigen is assayed by an in vitro T cell proliferation assay, and ELISPOT or intracellular staining and analysis by flow cytometry, for detection of cytokine production.

The presence of a T-cytotoxic cell response to the antigen is assayed by a CTL assay in vitro ($Cr^{51}$ release) or in vivo (Barber et al., *J. Immunol.*, 17: 27-31, 2003).

In another aspect, the invention relates to a method of screening immuno-therapeutic agents in vivo, the said method comprising the steps of:
  inducing a pathology, in the tissue of the multichimeric mouse as defined above,
  administering an immunotherapeutic agent to the said multichimeric mouse, and
  assaying for the therapeutic effect of the immunotherapeutic agent in the treated mouse.

The invention relates also to a method of screening vaccines in vivo, the said method comprising the steps of:
  administering a vaccine to the multichimeric mouse as defined above,
  inducing a pathology, in the tissue of the said multichimeric mouse, and
  assaying for the presence of an immunoprotective effect of the vaccine in the treated mouse.

The therapeutic effect of the immunotherapeutic agent or the immunoprotective effect of the vaccine, i.e. the effectiveness of the immunotherapeutic agent or of the vaccine, can be assessed with survival of the mouse, general status, and any other indices as suitable. These indices may comprise criteria which are specific of the pathology induced and which are well known to the person of skills in the art. For example, if the pathology is AML (acute myeloid leukemia), an assessment of the effectiveness of the immunotherapeutic agent or of the vaccine can be performed by numerating the number of AML cells in the bone marrow and the peripheral blood. The person of skills in the art will easily realize that it is also possible to monitor any side effects of the agent or the vaccine, should such side effects appear. Therefore, in a preferred embodiment, the two methods of the invention further comprise a step of assessing the side effects of the immunotherapeutic agent or of the vaccine, respectively. Preferably, the therapeutic effect and/or the side effects of the immunotherapeutic agent or the immunoprotective effect of the vaccine are assessed by comparison to a control. For example, the said control can be the multichimeric mouse of the invention which has not been treated.

According to a preferred embodiment of the preceding methods, the pathology is selected from the group consisting of: cancers, auto-immune diseases, and infectious diseases. The skilled person will realize that the said pathology can be induced by transplanting xenogenic cells carrying the pathology into the multichimeric mouse of the invention.

The cancer may be a solid-tumor or a liquid tumor. Examples of tumors which can be studied with the multichimeric mouse of the invention include carcinoma, including that of the bladder, breast, colon, head and neck, kidney, including renal cell carcinoma, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoactanthoma, seminoma, thyroid follicular cancer and teratocarcinoma, and other cancers yet to be determined.

The autoimmune disease is for example auto-immune diabetes. The infectious disease may be advantageously selected from the group consisting of: viral hepatitis, malaria, rubella, AIDS, Kreutzfeld-Jacob disease and EBV-associated cancers.

It is also an aspect of this invention to provide a method for testing the teratogenicity of stem cells. The said method comprises the steps of:
  transplanting the stem cells to be assessed in pregnant multichimeric mice of the invention, and
  monitoring fetal malformations.

The stem cells which are thus assessed may be any type of stem cells, including hematopoietic and non-hematopoietic stem cells. Preferably, the said stem cells are dedicated to be used in regeneration medicine. Teratogenicity tests are routinely performed in mice when testing new drugs in agreement with the guidelines of the health agencies and are thus well known to the skilled person.

It is also an aspect of this invention to provide a method for testing the tumorogenicity of cellular therapy, the said method comprising the steps of:
  transplanting the cells to be assessed in the multichimeric mouse of the invention, and
  detecting the apparition of tumors.

Methods for assaying the carcinogenicity have been used for numerous years. Such tests are mandatory for drug candidates the guidelines of the health agencies. The skilled person therefore has all the required information to perform the method of the invention.

The method of the invention may be used for mapping antigens, for screening new antigens and immunotherapeutic drugs, as well as for evaluating the immunogenicity of different antigen preparations for use as human vaccine and the efficiency of different drugs for use as immunotherapeutic in human.

According to yet another embodiment, the multichimeric mouse of the invention is useful for in vivo study of metabolism of administered compounds. In particular, the multichimeric mouse of the invention is useful for assaying the biological activity of the metabolites which are produced by the settled human cells, as well as the toxicity on the various organs of the murine model of these human specific metabolites.

In particular, it is possible to assess the potential toxicity of xenobiotic compounds with the multichimeric mouse of the invention. A "xenobiotic" as used herein refers to a chemical which is found in an organism but which is not normally produced or expected to be present in the said organism. Xenobiotics include most drugs (others than those compounds which naturally occur in the organism) and prodrugs, as well as other foreign substances.

It is known that one of the main causes of drug failure is toxicity resulting from drug metabolism by the liver. As a result, in vitro tests are routinely carried out for screening potentially harmful compounds. However, many of the liver models used for predicting the potential toxicity and/or biotransformations of the compounds have limitations. Much of the screening for metabolism and toxicity is done in primary human hepatocytes (cells isolated from normal liver) or human liver surrogates including animal hepatocytes and whole animals. Primary hepatocytes are problematic, since they do not divide significantly in culture and require constant fresh isolation. Toxicology studies performed in animals are occasionally misleading, because of differences existing between human patients and animal models.

On the other hand, it is possible to overcome the limitations of the previous liver models by using a multichimeric mouse according to the invention, the said multichimeric mouse comprising functional human hepatocytes. Such a multichimeric mouse can be obtained by e.g. using hepatic precursor cells as non-hematopoietic precursor cells. Methods for obtaining functional human hepatocytes in a chimeric mouse have been previously described (see e.g. WO 2005/067709). Such methods can be readily adapted to the present invention to produce a multichimeric mouse which comprises:
- a functional human SIRPα protein,
- functional transgenic human MHC class I and/or MHC class II molecules; the MHC class I and class II molecules may correspond to an haplotype which is identical or different to that of the transplanted hepatic precursor cells,
- a functional human immune system, which is restricted to the transgenic human MHC class I and/or MHC class II molecules solely,
- settled functional human hepatocytes,
- a lack of functional murine T lymphocytes, B lymphocytes and NK cells,
- a lack of murine MHC class I and MHC class II molecules cell surface expression, and
- a functional Alb-uPA transgene (urokinase-type plasminogen activator under the control of the albumin promoter) in the murine hepatocytes.

Alternatively, the said multichimeric mouse may comprise a FAh deletion, instead of the functional Alb-uPA transgene (Bissig et al., *J Clin Invest*, 120(3): 924-930, 2010).

The resulting multichimeric mouse allows the study of metabolic pathways following the administration of compounds. The said multichimeric mouse is important in particular for prodrugs, i.e., any compound that undergoes biotransformation prior to exhibiting its pharmacologic effects. Indeed, the human hepatocytes can produce metabolites, especially the active form of the drug, from the prodrugs, whereas the murine hepatocytes cannot do it.

Preferably, the said resulting multichimeric mouse is from a non-permissive background.

Thus, the invention provides a method for screening the in vivo metabolism of xenobiotic compounds in a multichimeric mouse of the invention, wherein said multichimeric mouse comprises settled human hepatocytes, said method comprising the steps of:
- administering the xenobiotic compound to be tested to the said multichimeric mouse in conditions allowing the said compound to interact with the settled human hepatocytes, and
- observing the biotransformation of the said compound by the said settled hepatocytes.

The xenobiotic is administrated into the multichimeric mouse according to all routes and all forms known to the person of skills in the art for the said drug. One condition in the administration is that the xenobiotic can interact with the settled hepatocytes.

The measurement of the level of the metabolites (degradation products), including intermediates and final products, enables to track the xenobiotic metabolism kinetics, including its half-life. The said multichimeric mouse enables also to observe the effects of the compound on the settled cells, to evaluate the doses at which the effects appear. Finally, it is possible to study the potential interactions between reactive metabolites and cellular macromolecules.

In the said particular multichimeric mouse of the invention, one could monitor the cytotoxic effects of the drug on the liver, e.g., by measuring the circulating hepatic transaminases and by analyzing the liver histology with optical microscopy techniques.

Some of the biological measurements described above require either the removing of the graft obtained as a result of the settlement of the human cells or the sacrifice of the animal, to provide access to the development and functioning of the settled cells. Therefore, the method of the invention can further comprise either a step of removing the graft from said non-human animal or the sacrifice of the non-human animal model harbouring settled heterologous nucleated cells capable of maintaining, differentiating and growing. This sacrifice can be carried out in a non-infected or infected animal, before or after the injection of an active or xenobiotic compound to be tested.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985);

Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames Et S. J. Higgins eds. 1984); Culture Of Animal Cells (R. I. Freshney, Alan R. Liss, Inc., 987); Immobilized Cells And Enzymes (IRL Press, 1986); B. Perbal, A Practical Guide To Molecular Cloning (1984); the series, Methods In Enzymology (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

The examples that follow are merely exemplary of the scope of this invention and content of this disclosure. One skilled in the art can devise and construct numerous modifications to the examples listed below without departing from the scope of this invention.

FIGURE LEGENDS

FIG. 1: Analysis of SIRPα expression on mC11b+ cells in three different transgenic founders.

Figure 2:
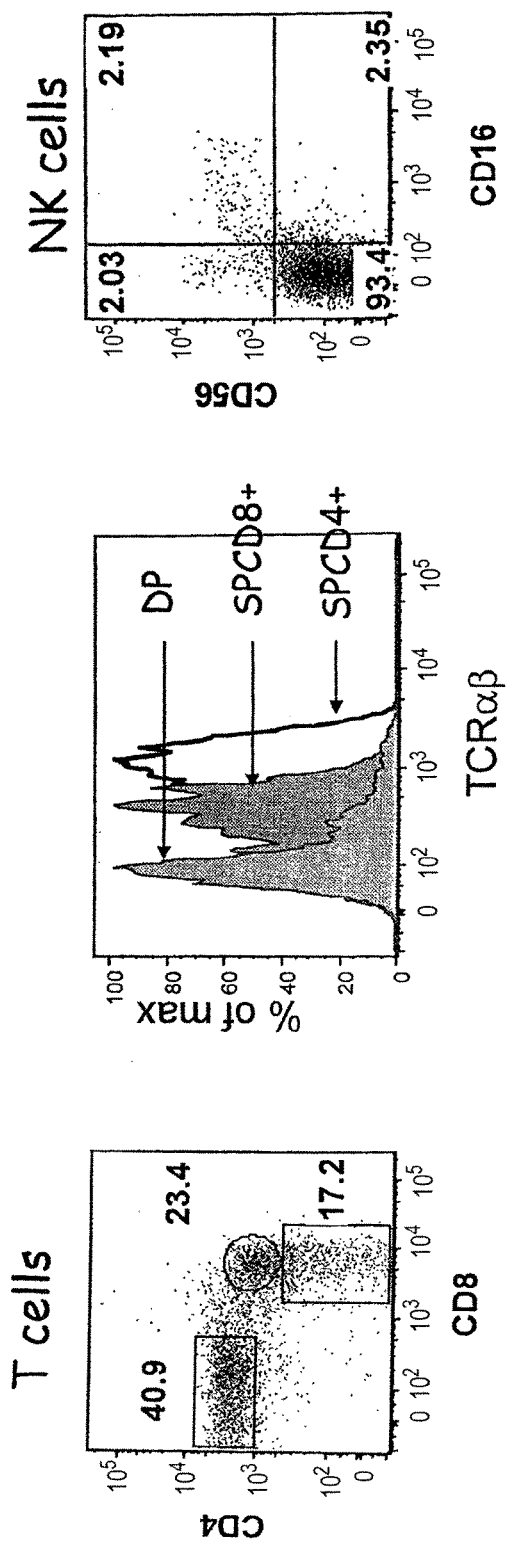

FIG. 2: Analysis of human T and NK cells in the thymus of the CH1-2hSa host 5 months after engraftment.

Figure 3:
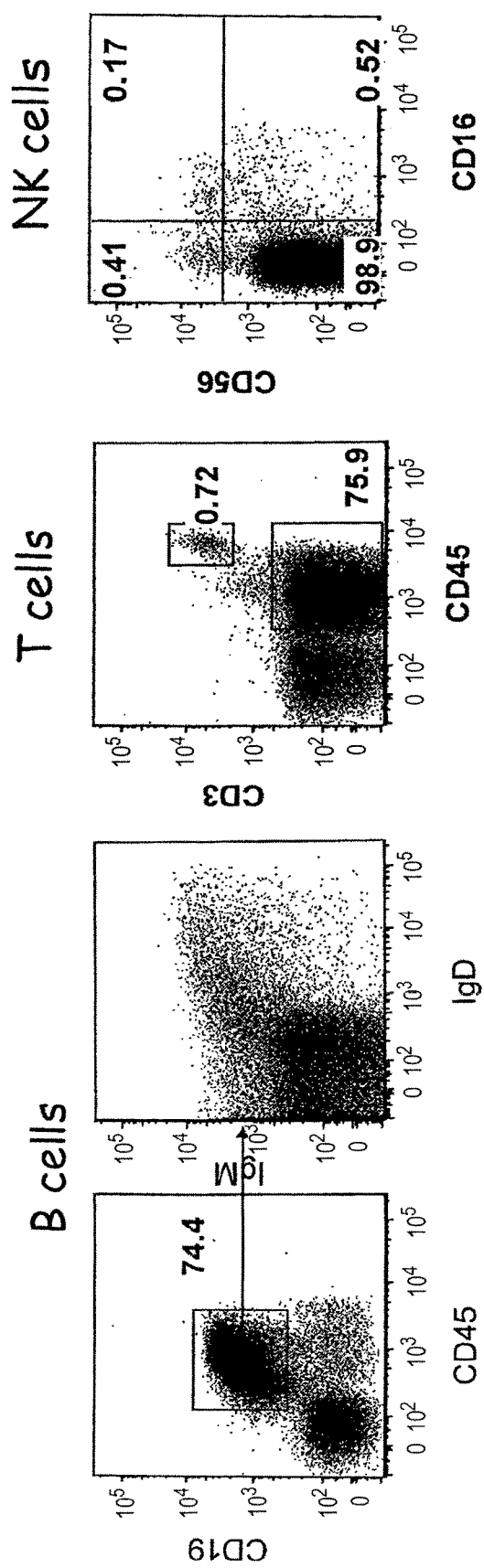

FIG. 3: Analysis of human lymphocytes in the bone marrow of the CH1-2hSa host 5 months after engraftment.

Figure 4:
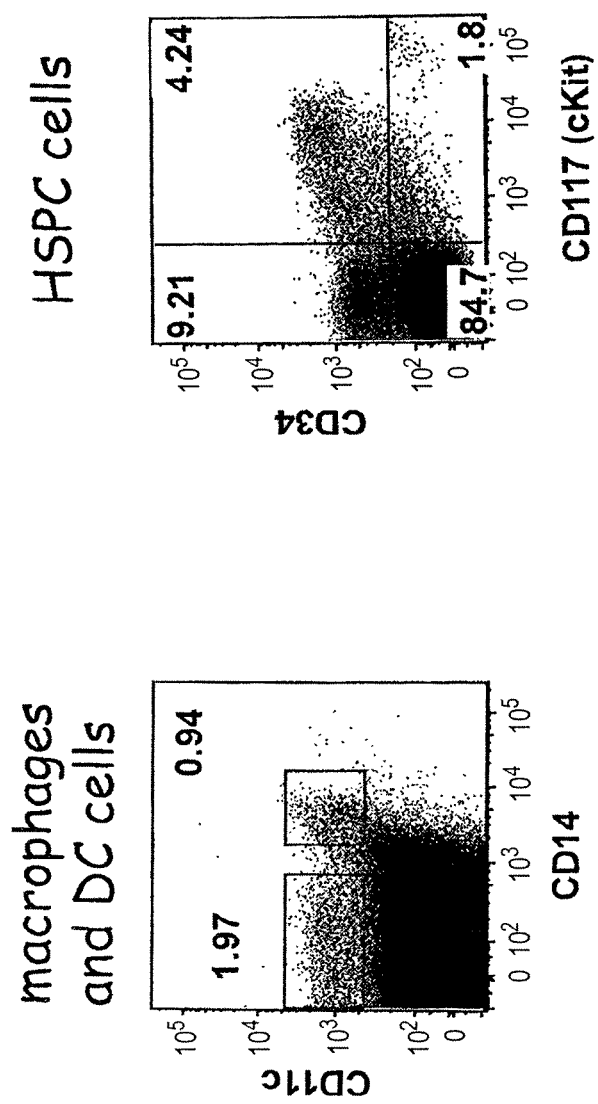

FIG. 4: Analysis of human myeloid cells (macrophages and dendritic cells, DC) and hematopoietic stem and progenitor cell (HSPC) in the bone marrow of the CH1-2hSa host 5 months after engraftment.

Figure 5:
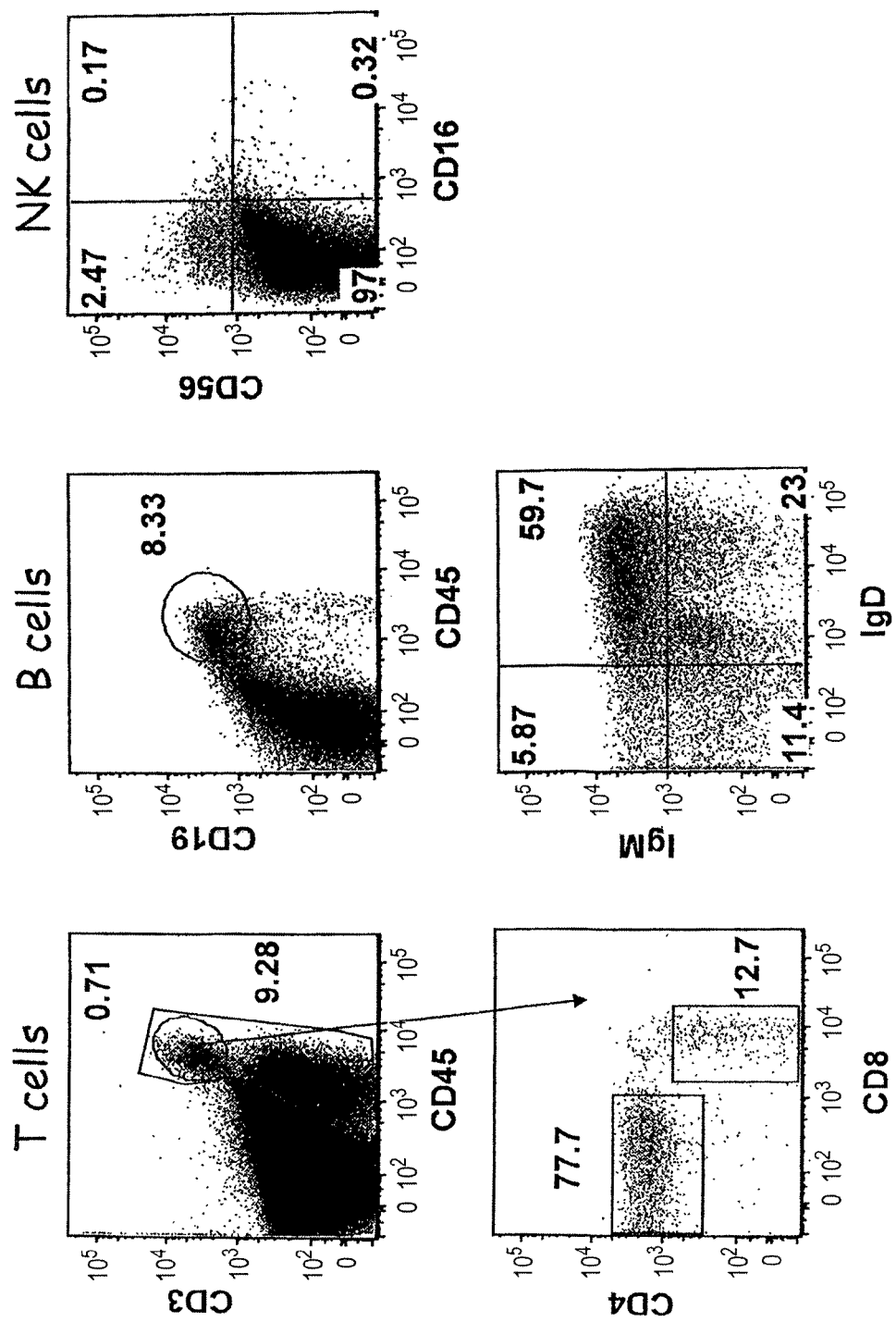

FIG. 5: Analysis of human lymphocytes subsets in the spleen of the CH1-2hSa host 5 months after engraftment.

FIG. 6: Amino acid sequence of the human SIRPα protein.

FIG. 7: Nucleotide sequence of the human SIRPα gene.

Figure 8:
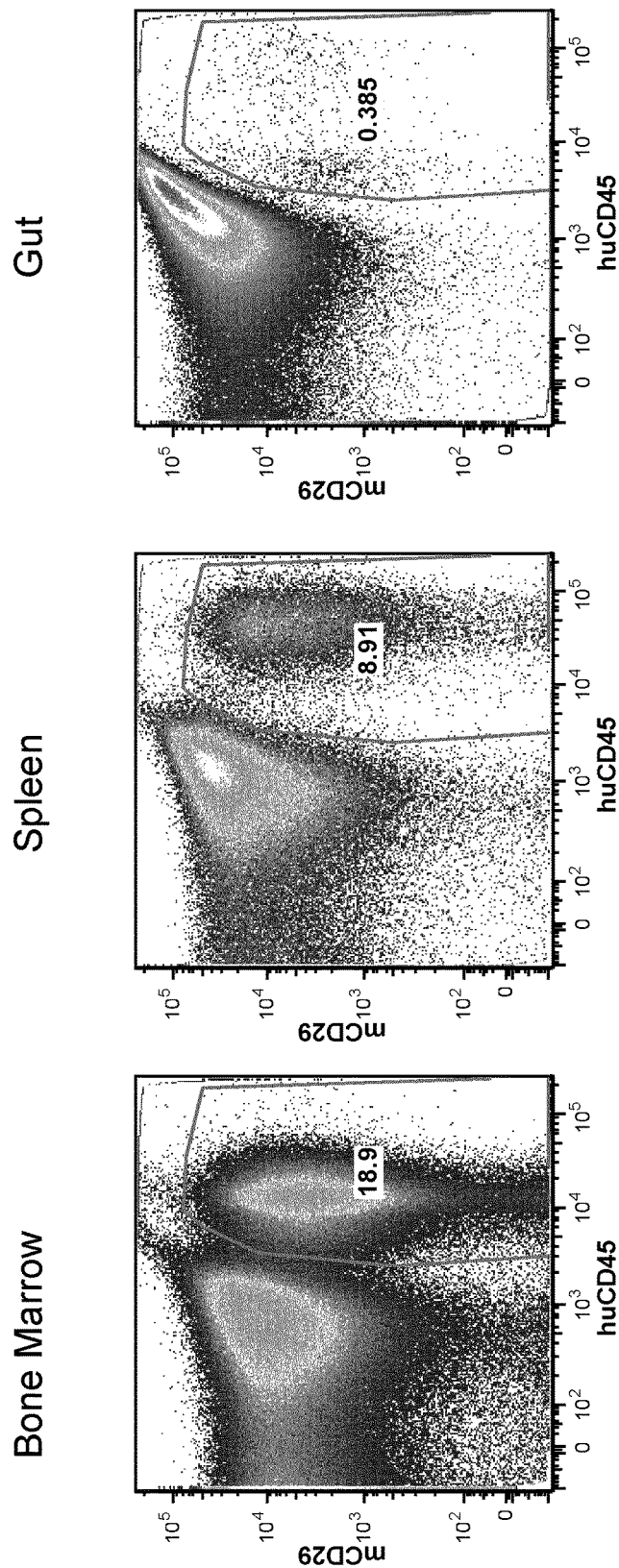

FIG. 8: Analysis of the presence of human T, B and NK cells in the bone marrow, spleen and gut of the CH1-2hSa host 6 months after engraftment (gated on human $CD45^+$ cells).

Figure 9:
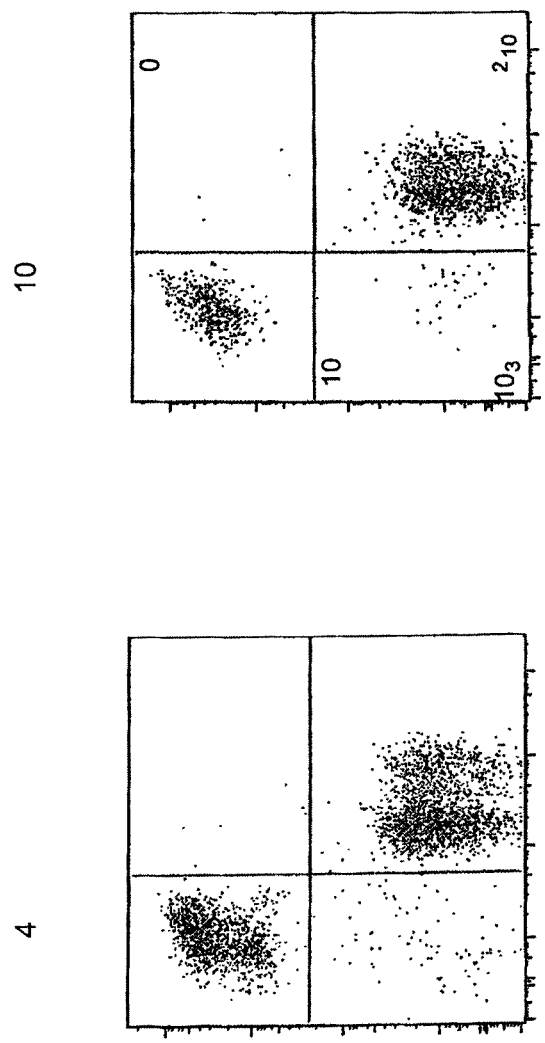

FIG. 9: Analysis of reconstitution efficiency in CH12hSa and NSG hosts (gated on human $CD45^+$ cells).

Figure 10:
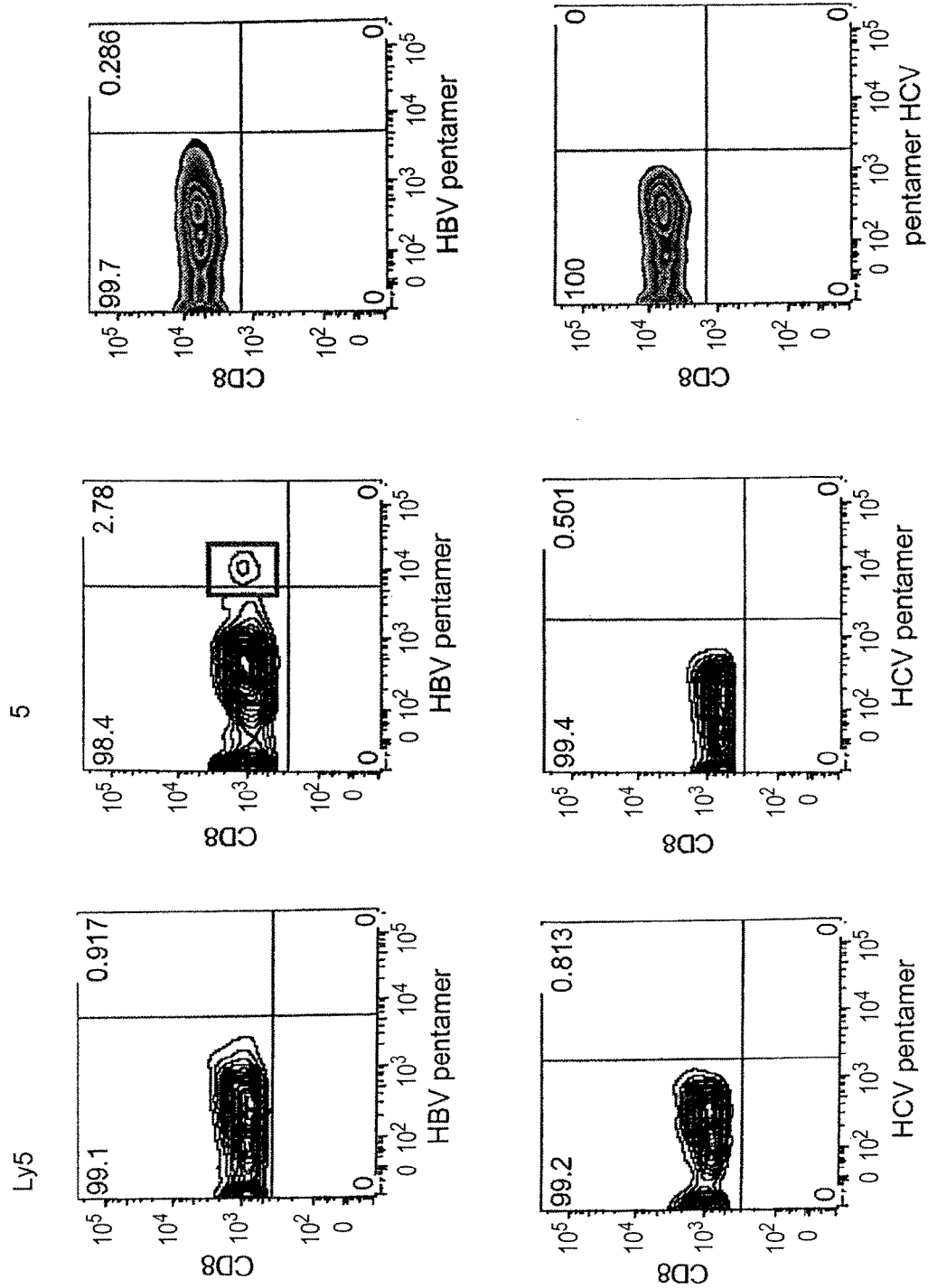

FIG. 10: HLA-A2 restricted anti-HBV human CD8 T cells responses upon vaccination of CH12hSa chimera.

Figure 11:
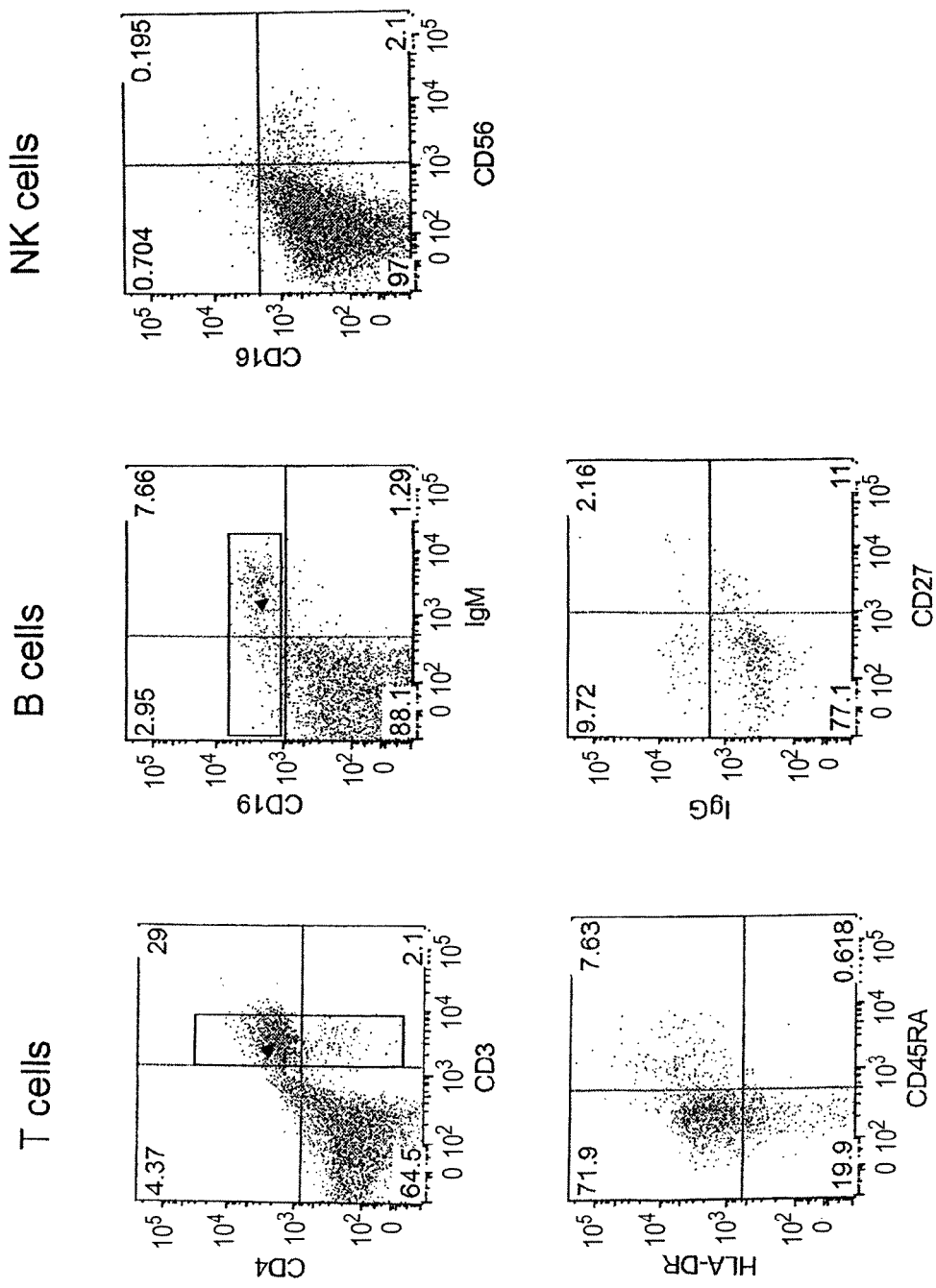

FIG. 11: Analysis of the migration of human T, B and NK cells to the liver of the CH1-2hSa host 6 months after engraftment (gated on human $CD45^+$ cells).

EXAMPLES

Mouse Genetic Background

The CH1-2 mice derived from the crossing of 129 ($Rag2^{-/-}$ $\gamma c^{-/-}$, $C5^{-/-}$) X FVB ($HLA-DR1^+$, $C5^{-/-}$) X B6 ($\beta2m^{-/-}$, $I-A\beta^{b-/-}$, HLA-A2±) laboratory inbred mouse strains as described in WO 2008/010099 and WO 2008/010100. More precisely, the $Rag2^{-/-}$, $\gamma_c^{-/-}$ mice (129 background) were crossed with $I-A\beta^{b-/-}$ (C57B1/6 background) and the F1 progeny were crossed successively with $\beta_2m^{-/-}$ (C57B1/6 background), HLA-DR1 transgenic mice ($DR1^+$, FVB background) and HLA-A2.1 transgenic mice. $I-A\alpha^{b+}$ (essential for murine MHC class $II^{-/-}$ phenotype) and $C5^{-/-}$ progenies (both 129 and FVB strains are constitutively $C5^{-/-}$) were selected from each crossing.

FVB, 129 and B6 are well defined backgrounds which are well known to the person of skills in the art (Ridgway et al., Nature Immunol; 8: 669-673, 2007). Among these strains, the 129 strain was used for its ability to be transgenized and give rise to ES cells. FVB strain was used because its fertilized eggs contain large and prominent pronuclei, which facilitate the microinjection of DNA during transgenesis, and because they survive much better than pure B6 eggs. FVB and B6 backgrounds were used for their vigorous reproductive performance with large litters.

Transgenesis

The hCD172 cDNA encoding the membrane receptor SIRPα (accession number NM_001040022) was introduced downstream a 7.2 Kb sequence corresponding to the murine c-fms promoter. All the parts were cloned into a pGL2B vector. The resulting 11 kb construct was purified on agarose gel.

Superovulated CH1-2 3-week females were mated with CH1-2 males. Unicellular embryos were then microinjected with the construct (in collaboration avec F. Langa, IP). This procedure avoids the generation of mosaic mice upon transgenesis. Transfected embryos were then implanted into the recipient mice. Twenty-five newborn mice were obtained, of which 11 (4 males and 7 females) tested positive by PCR, indicating that the transgene had integrated into their genome Expression of a SIRPα Transgene by $Rag^{-/-}$ $\gamma c^{-/-}$ $\beta 2m^{-/-}$ $IA-\beta^{b-/-}$ $HLA-A2^+$ $HLA-DR1^+$ Mice Some of these animals were then checked by flow cytometry for human SIRPα expression at the surface of macrophages in the periphery (double staining for hCD172 and mCD11b—expressed on murine macrophages surface). All transgenic founders were found by flow cytometry to express homogeneously SIRPα. FIG. 1 shows 3 mice expressing the hCD172 transgene on most of the $mCD11b^+$ cells. Expression of the human hSIRPα receptor was detected in both macrophages ($CD11b^+$) and dendritic cells ($CD11c^+$) and some $GR1^+$ cells.

The transgenized mice were immediately mated. The resulting new-born mice were irradiated and then grafted intra-hepatically with hematopoietic precursor cells of human blood chord. The level of reconstitution found in human SIRPα transgenic hosts engrafted with human hematopoietic progenitors is comparable if not superior to that of NOD SCID $\gamma c^{-/-}$ (NSG) hosts, showing high levels of T, B, NK and myeloid cells.

Hematopoietic reconstitution in $Rag^{-/-}$ $\gamma c^{-/-}$ $\beta 2m^{-/-}$ $IA-\beta^{b-/-}$ $HLA-A2^+$ $HLA-DR1^+$ $huSIRP\alpha^+$ mice (CH1-2huSa)

Newborn CH1-2huSa mice were first irradiated, then intra-hepatically grafted with human cord blood $CD34^+$ hematopoietic progenitors. The reconstitution by human hematopoietic cells ($CD45^+$ cells population targeted upstream in order to exclude Ly5.2+ murine cells) was monitored by flow cytometry 5 months after engraftment.

As shown in FIG. 2, human thymocytes developed normally in the murine CH1-2huSa thymic environment. Both $CD8^-CD4^-$ (DN) and $CD8^+CD4^+$ (DP) immature thymocytes and $CD4^+CD8^-$ (SPCD4) and $CD8^+CD4^-$ (SPCD8) mature thymocytes were present. As expected, only the SP4 and SP8 populations showed a high level of TCRaB expression, thus confirming their maturity. Likewise, $CD56^+$, $CD56^+$ $CD16^+$ and $CD16^+$ NK cells were detected.

Human B cells ($CD19^+$) were present in the chimera bone marrow with an IgM IgD expression profile similar to the one of cells engaged in development (FIG. 3). Human CD3$^+$ T cells were also detected in the chimera bone marrow as well as CD56$^+$, CD56$^+$CD16$^+$ and CD16$^+$ NK cells.

Macrophages and dendritic cells were detected in the bone marrow by co-staining for CD11c and CD14 (FIG. 4). Interestingly, a population of CD34+ cells was identified in the chimera bone marrow. These cells could correspond to the maintenance in chimera marrow of a population of human hematopoietic precursor cells (CD34$^+$±CD117$^+$).

As shown in FIG. 5, CD3$^+$ CD4$^+$ and CD3$^+$ CD8$^+$ human T cells, and CD19$^+$ human B cells with an IgM IgD profile similar to mature human B cells, and human NK cells (mostly CD56$^+$ CD16$^+$) were detected.

Presence of Human T, B and NK Cells to the Bone Marrow, Spleen and Gut of CH1-2hSa Chimeras CH1-2hSa irradiated newborns were engrafted intra-hepatically with 50 000 CD34$^+$ human cord blood hematopoietic progenitors. Five month later, the percentages of human huCD45$^+$ mCD29$^-$ hematopoietic cells were evaluated by flow cytometry (gated on CD45$^+$ cells) in the bone marrow, the spleen and the gut.

As shown on FIG. 8, human cells were found in the 3 sites, indicating that they were able to move through the circulation to other organs, including lymphoid organs.

Differential Ability of CH12 Versus RAG$^{-/-}$ γc$^{-/-}$ Murine Thymic Anlage at Inducing the Development of Mature Human T Cells.

Fetal thymuses from either CHb12 or RAG$^{-/-}$ γc$^{-/-}$ HLA-mice were seeded with human cord blood CD34$^+$ hematopoietic progenitors in the presence of human factors. At the end of the Fetal Thymic Organ Culture (FTOC), human CD45$^+$ CD4$^+$ and CD8$^+$ cells were analyzed for the expression CD3 as marker of maturity. As shown in the table below, HLA expression dramatically increases the % of mature CD4 and CD8 human T cells in the thymus of chimera.

Thymus were removed from day 14 embryos and each thymic lobe was incubated in Terasaki wells for 2 days in 25 μl of complete medium: RPMI 1640 supplemented with 10% heat-inactivated human serum, 5% fetal calf serum, 100 IU/ml penicillin, 100 μg/ml streptomycin, 2 mml-glutamine. 10-30 000 CD34$^+$ cells purified from cord blood were added to each well. The plates were immediately inverted to allow the formation of hanging drops and incubated undisturbed in a humidified incubator (5% CO$_2$ in air, 37° C.). After 48 h, thymic lobes were transferred onto floating nucleopore filters (Isopore membrane, 25 mm in diameter, pore size 8 μm, Millipore SA, France) in six-well plates in 2.5 ml of complete medium and cultured for 28-35 days at 37° C. in air supplemented with 5% CO$_2$ with a weekly medium change. Cytokines [rhu-IL-2 (5 ng/ml), 20 ng/ml rhu-IL-7 and 50 ng/ml rhu-SCF] were included only during the first 48 h, mainly to prevent apoptosis of the human progenitors and of early T-cell progenitors. Cells were then extracted from the different lobes by mechanical disruption of the lobes, and were pooled to be analyzed by flow cytometry.

Results

| Origin of fetal thymi | Human CD4$^+$ CD3+ cells (%) | Human CD8$^+$ CD3$^+$ cells (%) |
|---|---|---|
| CH12 | 23 | 54 |
| RAG$^{-/-}$ γc$^{-/-}$ | 4 | 13 |

Ig Production by Reconstituted CH12hSa Chimera: Differential Ability of CH12hSa Versus RAG$^{-/-}$ γc$^{-/-}$ Reconstituted Chimera at Inducing the Production of Human Ig Serum from either CH12hSa or NOD SCID γc$^{-/-}$ reconstituted with human cord blood CD34$^+$ hematopoietic progenitors were tested for the presence of both human IgM and human IgG. As shown in the table below, IgM titer was strongly increased in CH12hSa chimera compared with NOD SCID γc$^{-/-}$ chimera. Importantly, IgG were only detected in CH12hSa chimera.

| Chimera strain | IgM (ng/ml) | IgG (ng/ml) |
|---|---|---|
| CH12hSa | 818 | 165 |
| NOD SCID γc$^{-/-}$ | 116 | — |

Comparison of reconstitution efficiency between CH12hSa and NSG hosts.

CH1-2hSa and NOD SCID γc$^{-/-}$ (NSG) irradiated newborns were engrafted intra-hepatically with 50 000 CD34$^+$ human cord blood hematopoietic progenitors. Seven weeks later, the percentages of human huCD45$^+$ Ly5$^-$ hematopoietic cells were evaluated by flow cytometry (gated on CD45$^+$ cells).

As shown on FIG. 9, CH1-2hSa host reconstitution by human cells is higher than the reconstitution of NSG host reconstitution.

Validation of CH12hSa Chimera for the Test of Vaccine Candidates

CH1-2 chimeras transgenic for human SIRPalpha were used for vaccination experiment 5 months after engraftment.

Eight chimeras were injected with cardiotoxin intramuscularly.

Five days later, 4 chimeras were injected intramuscularly with HBV (capsid and env) DNA: the vectors used were pCMV-HBc and pCMV-S2S (Michel et al., Proc. Natl. Acad. Sci. USA, 92: 5307-5311, 1995; Deng et al., Hepatology, 50(5): 1380-1391, 2009) Two weeks later, the injected chimera were reboosted intraperitoneally with a mixture of HBV proteins: HBsAg (env)+(capsid) HBcAg in Alu-S-gel. As control, the 4 left chimera were injected twice with PBS.

Two weeks after the last injection, the chimera were sacrificed and the CD8 anti-HBV HLA-A2 restricted specific T cell response was measured (gated on CD45$^+$ CD8$^+$ CD3$^+$ cells) by staining using a mixture of env and core HLA-A2 pentamers (FIG. 10).

As a control, irrelevant staining using HCV protein HLA-A2 pentamers was performed.

The results were expressed as % of pentamer$^+$ cells among the total human CD8$^+$ T cells.

As shown on FIG. 10, vaccinated chimeras were able to mount specific anti-HBV HLA-A2 CD8 T cell response.

No anti-HCV response were detected, neither in vaccinated nor in naïve cord blood CD8 T cells, indicating that the response was specific for HBV. In contrast, no response could be detected in the absence of vaccination, further emphasizing the specificity of the response.

CD8 HLA-A2-restricted HBV specific T cells were detected in the spleen of CH1-2hSa chimeras reconstituted with HLA-A2$^+$ CB CD34$^+$ human progenitor upon DNA and protein vaccination against both envelop and capsid HBV antigens. CH1-2hSa chimeras are thus capable of mounting CD8-specific T cell response to vaccination in a HLA-restricted manner.

Migration of Human T, B and NK Cells to the Liver of CH1-2hSa Chimeras

CH1-2hSa chimeras were engrafted with human CD34+ cord blood hematopoietic progenitors. Five months later, the presence of T, B and NK cells were assessed in the liver of the chimera by flow cytometry (gated on CD45+ cells).

The 3 subsets were present, indicating that they were capable of migrating to the liver independently of vaccination of CH1-2hSa chimeras. The liver T cells were found to exhibit an activated CD45RAlow HLA-DR+ activated phenotype (FIG. 11).

The invention claimed is:

1. A transgenic mouse, said mouse having a genome comprising:
    a) a genetic background that is FVB/N, C57Bl/6, 129, or C3H, or a mixture of at least two genetic backgrounds selected from the group consisting of FVB/N, C57Bl/6, 129, and C3H; and
    b) a transgene encoding human SIRPα, wherein the human SIRPα is functionally expressed in the mouse;
    c) an inactivated β2-microglobulin (β2-m) gene, wherein the mouse does not express functional major histocompatibility complex (MHC) I proteins;
    d) an inactivated I-Aβ$^b$ gene, wherein the mouse does not express functional MHC II proteins;
    e) a homozygous disruption of a Rag2 gene (Rag2$^{-/-}$) and a homozygous disruption of a common receptor γ ($γ_c^{-/-}$) gene, wherein the mouse lacks functional mouse T lymphocytes, B lymphocytes, and natural killer NK cells;
    f) a transgene encoding a human MHC I protein and a transgene encoding a human MHC II protein, wherein the mouse functionally expresses the human MHC I and II proteins; and
    wherein said transgenic mouse supports development of human myeloid and lymphoid lineages comprising T cells, B cells, NK cells, macrophages and dendritic cells following engraftment of human cord blood hematopoietic stem cells (HSCs).

2. A transgenic mouse of claim 1, where the inactivated β2-microglobulin gene is a homozygous disruption of the β2-microglobulin gene ($β_2m^{-/-}$).

3. The transgenic mouse of claim 1, wherein the inactivated I-Aβ$^b$ gene is a homozygous disruption of an H-2$^b$-Aβ gene (H-2$^b$-Aβ$^{-/-}$).

4. The transgenic mouse of claim 1, wherein the MHC I protein is human leukocyte antigen (HLA) A2 (HLA-A2) and the MHC II protein is HLA-DR1.

5. The transgenic mouse of claim 1, wherein said mouse has a genotype of Rag2−/−, $β_2$-m$^{-/-}$, $γ_c^{-/-}$, and I-Aβ$^{b-/-}$, and optionally HLA-A2$^{+/+}$and/or HLA-DR1$^{+/+}$.

6. The transgenic mouse of claim 1, wherein said mouse does not express a functional C5 protein.

7. The method of producing a transgenic mouse comprising human myeloid and lymphoid lineages comprising T cells, B cells, and NK cells, macrophages and dendritic cells, said method comprising transplanting human cord blood HSCs into the transgenic mouse of claim 1.

8. The transgenic mouse comprising human myeloid and lymphoid lineages comprising T cells, B cells, NK cells, macrophages and dendritic cells made by the method of claim 7.

* * * * *

UNITED STATES PATENT AND TRADEMARK OFFICE
CERTIFICATE OF CORRECTION

PATENT NO. : 9,894,888 B2  
APPLICATION NO. : 14/388108  
DATED : February 20, 2018  
INVENTOR(S) : Sylvie Garcia et al.

Page 1 of 1

It is certified that error appears in the above-identified patent and that said Letters Patent is hereby corrected as shown below:

In the Claims

Claim 1, Line 34:
"A transgenic mouse, said mouse having a genome",
Should read:
--A transgenic mouse, having a genome--

Claim 7, Line 49:
"The method",
Should read:
--A method--

Claim 7, Line 51:
"B cells, and NK cells",
Should read:
--B cells, NK cells--

Claim 8, Line 54:
"The transgenic mouse",
Should read:
--A transgenic mouse--

Signed and Sealed this  
Twenty-fourth Day of July, 2018

Andrei Iancu  
*Director of the United States Patent and Trademark Office*